United States Patent [19]

Benet et al.

[11] Patent Number: 6,004,927
[45] Date of Patent: Dec. 21, 1999

[54] METHOD FOR INCREASING BIOAVAILABILITY OF ORALLY ADMINISTERED PHARMACEUTICAL COMPOUNDS

[75] Inventors: Leslie Benet, Belvedere; Chi Yuan Wu, San Francisco, both of Calif.

[73] Assignee: Regents of the University of California, Oakland, Calif.

[21] Appl. No.: 08/462,757

[22] Filed: Jun. 5, 1995

Related U.S. Application Data

[62] Division of application No. 08/190,288, Feb. 2, 1994, Pat. No. 5,567,592.

[51] Int. Cl.⁶ ............... A61K 31/015; A61K 31/12; A61K 31/13; A61K 38/12
[52] U.S. Cl. ............... 514/9; 514/506; 514/557; 514/579; 514/675; 514/693; 514/764; 514/946
[58] Field of Search ............... 424/450, 452, 424/465; 514/9, 11, 772, 784, 788, 946, 764, 693, 675, 579, 557, 506

[56] References Cited

U.S. PATENT DOCUMENTS

| | | | |
|---|---|---|---|
| 3,862,308 | 1/1975 | Schmitt et al. | 424/54 |
| 4,751,220 | 6/1988 | Parker et al. | 514/29 |
| 4,822,816 | 4/1989 | Markham | 514/474 |
| 4,849,227 | 7/1989 | Cho | 424/498 |
| 4,944,949 | 7/1990 | Story et al. | 424/451 |
| 4,968,716 | 11/1990 | Markham | 514/474 |
| 5,070,085 | 12/1991 | Markham | 514/161 |
| 5,124,330 | 6/1992 | King | 514/250 |
| 5,156,842 | 10/1992 | Mulligan | 424/195.1 |
| 5,179,122 | 1/1993 | Greene et al. | 514/458 |
| 5,284,657 | 2/1994 | Lu et al. | 424/435 |
| 5,288,499 | 2/1994 | Janoff et al. | 424/450 |
| 5,332,747 | 7/1994 | Van Dyke | 514/280 |
| 5,350,756 | 9/1994 | Smith | 514/289 |
| 5,359,030 | 10/1994 | Ekwuribe | 530/303 |
| 5,366,980 | 11/1994 | Smith | 514/289 |
| 5,409,690 | 4/1995 | Howell et al. | 514/34 |
| 5,411,947 | 5/1995 | Hostetler et al. | 514/43 |
| 5,422,350 | 6/1995 | Woolf | 514/252 |

(List continued on next page.)

FOREIGN PATENT DOCUMENTS

| | | |
|---|---|---|
| 0 127 677 | 8/1990 | European Pat. Off. . |
| 2 706 771 | 12/1994 | France . |
| WO90/12583 | 11/1990 | WIPO . |
| WO92/06680 | 4/1992 | WIPO . |

OTHER PUBLICATIONS

Jachez, B., et al., "Restoration of Taxol Sensitivity of Multidrug–Resistant Cells by the Cyclosporine SDZ PSC 833 and the Cyclopeptide SDZ 280–446," *J. Natl. Can. Inst.*, 85(6):478–483 (1993).

Chervinsky, D.S., et al., "Cremphor–EL Enhances Taxol Efficacy in a Multi–Drug Resistant C1300 Neuroblastoma Cell Line," *Anticancer Research*, 13:93–96 (1993).

Webster, L., et al., "Measurement of Cremphor EL Following Taxol: Plasma Levels Sufficient to Reverse Drug Exclusion Mediated by the Multidrug–Resistant Phenotype," *J. Natl. Can. Inst.*, 85(20):1685–1690 (1993).

(List continued on next page.)

*Primary Examiner*—Jeffrey E. Russel
*Attorney, Agent, or Firm*—Cooley Godward LLP

[57] ABSTRACT

A method for increasing bioavailability of an orally administered hydrophobic pharmaceutical compound, which comprises orally administering the pharmaceutical compound to a mammal in need of treatment with the compound concurrently with a bioenhancer comprising an inhibitor of a cytochrome P450 3A enzyme or an inhibitor of P-glycoprotein-mediated membrane transport, the bioenhancer being present in sufficient amount to provide bioavailability of the compound in the presence of the bioenhancer greater than the bioavailability of the compound in the absence of the bioenhancer.

18 Claims, 2 Drawing Sheets

U.S. PATENT DOCUMENTS

| | | | |
|---|---|---|---|
| 5,424,289 | 6/1995 | Yang et al. | 514/12 |
| 5,436,243 | 7/1995 | Sachs et al. | 514/231.8 |
| 5,455,286 | 10/1995 | Amidon et al. | 523/122 |
| 5,466,696 | 11/1995 | Woolf | 514/297 |
| 5,616,608 | 4/1997 | Kinsella et al. | 514/449 |
| 5,643,909 | 7/1997 | Pfister et al. | 514/253 |
| 5,648,506 | 7/1997 | Desai et al. | 549/510 |
| 5,652,212 | 7/1997 | Cavanak et al. | 514/11 |

OTHER PUBLICATIONS

Adams, M.W., d–Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical technology, Paris, Jun. 2–4, 1992.

Albengres et al., "Cyclosporin and Ketoconazole, Drug Interaction or Therapeutic Association?", International Journal of Clinical Pharmacology et al., 30(12): 555–570, 1992.

Akitoshi et al., Abstract "Acceleration of Transdermal Absorption of Pharmaceuticals by Essential Oils and Organic Solvents", Chem. Abst., 112:125228t, 1990.

Arias, I.M. et al., "Structure & Function of P–Glycoprotein in the Normal Liver", Xenobiotics and Cancer (L. Ernster et al., eds.), Japan Sci. Soc. Press, Tokyo/Taylor & Francis, Ltd., London, pp. 229–239, 1991.

Baciewicz et al., "Ketoconazole and Fluconazole Drug Interactions", Archives of Internal Medicine, 153(17):1970–76, 1993.

Back et al., "Comparative Effects of two Antimycotic Agents, Ketoconazole and Terbinafine on the Metabolism of Tolbutamide, Ethinyloestradiol, Cyclosporin and Ethoxycoumarin by Human Liver Microsomes In Vitro", British Journal of Clinical Pharmacology, 28:166–170, 1989.

Back et al., "Azoles, Allylamines and Drug Metabolism", British Journal of Dermatology, Supplement 39, 126:14–18, 1992.

Back, David J., and Orme, Michael L'E.; "Pharmacokinetic Drug Interactions with Oral Contraceptives", (1990) Clin. Pharmacokinet. 18(6):472–484.

Bonkovsky et al., "Cytochrome $P_{450}$ of Small Intestinal Epithelial Cells", Gastroenterology, 88:458–467 (1985).

Callaghan, Richard and Riordan, John R.; "Synthetic and Natural Opiates Interact with P–glycoprotein in Multidrug–resistant Cells", (1993) J. Biol. Chem. 268(21):16059–16064.

Chan et al., "Drug Interactions with Cyclosporine: Focus on Antimicrobial Agents", Clinical Transplantation, 6:(3)(1):141–153, Jun. 1992.

Chang, Tammy et al., "The Effect of Water–Soluble Vitamin E on Cyclosporine Pharmacokinetics in healthy Volunteers", Abstract in American Society to Clinical Pharmacology and Therapeutics, 57(2):163, Feb. 1995.

Clynes, Martin; "Cellular Models for Multiple Drug Resistance in Cancer", (1993) In Vitro Cell. Dev. Biol. 29A:171–179.

de Smet et al., "Combined use of Cyclosporine and Ketoconazole in the treatment of Endogenous Uveitis", American Journal of Ophthalmology, 113:687–690, Jun. 1992.

Endicott, Jane A., and Ling, Victor; "The Biochemistry of P–glycoprotein–mediated Multidrug Resistance", (1989) Annu. Rev. Biochem. 58:137–171.

Fahr, Alfred; "Cyclosporin Clinical Pharmacokinetics" (1993) Clin. Pharmacokinetic 24(6):472–495.

Fairchild, Craig R., and Cowan, Kenneth H.; "Keynote Address: Multidrug Resistance: A Pleiotropic Response To Cytotoxic Drugs" (1991) Int. J. Radiation Oncology Biol. Phys. 20:361–367.

Fasco, Michael J. et al.; "Rat Small Intestinal Cytochromes P450 Probed by Warfarin Metabolism" (1993) Mol. Pharmacol. 43:226–233.

First et al., "Concomitant Administration of Cyclosporin and Ketoconazole in Renal Transplant Recipients", The Lancet, 2:1198–1201, Nov. 18, 1989.

First et al., "Cyclosporine Dose Reduction by Ketoconazole Administration in Renal Transplant Recipients", Transplantation, 51(2):365–370, Feb. 1991.

Fojo, Antonio T.; "Multidrug Resistance" (1991) Adv. Intern. Med. 36:195–218.

Gatmaitan, Zenaida C. and Irwin M. Arias; "Structure and Function of P–Glycoprotein in Normal Liver and Small Intestine" (1993) Adv. Pharmacol. 24:77–97.

Greenblatt. David J.; "Presystemic Extraction: Mechanisms and Consequences" (1993) J. Clin. Pharmacol 33:650–656.

Hait, William N. et al.; "Terfenadine (Seldane®):A New Drug for Restoring Sensitivity to Multidrug Resistant Cancer Cells" (1993) Biochem. Pharmacol 45:401–406.

Hebert, Mary F. et al.; "Bioavailability of Cyclosporine with Concomitant Rifampin Administration is Markedly Less Than Predicted by Hepatic Enzyme Induction" (1992) Clin. Pharmacol. Ther. 52:453–457.

Henricsson et al., "Cyclosporin Metabolism in Human Liver Microsomes and its Inhibition by Other Drugs", Pharmacology & Toxicology, 66:49–52, 1990.

Hsing, Shu et al.; "The Function of Gp170, the Multidrug–Resistance Gene Product. in the Brush Border of Rat Intestinal Mucosa" (1992) Gastroenterology 102:879–885.

Hunter, J. et al., "Epithelial Secretion of Vinblastine by Human Intestinal Adenocarcinoma Cell (HCT–8 and T84) Layers Expressing P–Glycoprotein", British Journal of Cancer, 64:437–444, 1991.

Hunter, Janice et al.; "Functional Expression of P–glycoprotein in Apical Membranes of Human Intestinal Caco–2 Cells" (1993) J. Biol. Chem. 268:14991–14997.

Jancis, Erik M. et al.; "Estradiol Induction of Rhodamine 123 Efflux and the Multidrug Resistance Pump in Rat Pituitary Tumor Cells" (1993) Mol. Pharmacol. 43:51–56.

Kaminsky, Laurence, and Michael J Fasco; "Small Intestinal Cytochromes P450" (1992) Toxicology 21(6):407–422.

Kolars, Joseph C. et al.; "Identification of Rifampin–inducible P450IIIA4 (CYP3A4) in Human Small Bowel Enterocytes" (1992) J. Clin. Invest. 90:1871–1878.

Kolars, Joseph C. et al.; "Heterogeneity of Cytochrome P450IIIA Expression in Rat Gut Epithelia" (1992) Gastroenterology 102:1186–1198.

Kolars, Joseph C. et al.; "Cyclosporine Metabolism by P450IIIA in Rat Enterocytes—Another Determinant of Oral Bioavailability?" (1992) Transplantation 53:596–602.

Komori, Masayuki et al.; "Cytochrome P–450 in Human Liver Microsomes: High–Performance Liquid Chromatographic Isolation of Three Forms and Their Characterization" (1988) J. Biochem. 104:912–916.

Kralovanszky, et al.; "Isolation of Viable Intestinal Epithelial Cells and Their Use for in Vitro Toxicity Studies", In Vivo 4:201–204, 1990.

Kronbach, Thomas et al.; "Cyclosporine Metabolism in Human Liver: Identification of a Cytochrome P450III Gene Family as the Major Cyclosporine Metabolizing Enzyme Explains Interactions of Cyclosporine With Other Drugs" (1988) Clin. Pharmacol. Ther. 43:630–635.

Kronbach, Thomas et al.; "Oxidation of Midazolam and Triazolam by Human Liver Cytochrome P450IIIA4" (1989) Molec. Pharm. 36:89–96.

Lalka et al.; "The Hepatic First–Pass Metabolism of Problematic Drugs" (1993) J. Clin. Pharmacol. 33:657–669.

Ludescher et al.; "Rapid Functional Assay for the Detection of Multidrug–Resistant Cells Using the Fluorescent Dye Rhodamine 123 (Letter; Comment)" (1991) Blood 78(5):1385–1387.

Ludescher et al.; "Detection of Activity of P–Glycoprotein in Human Tumor Samples Using Rhodamine 123" (1992) Br. J. Haematol 82:161–168.

Lum et al.; "Clinical Trials of Modulation of Multidrug Resistance. Pharmacokinetic and Pharmacodynamic Considerations" (1993) Cancer 72:3502–3514.

Lum et al.; "Molecular Targets in Oncology: Implications of the Multidrug Resistance Gene" (1993) Pharmacotherapy, 13:88–109.

Muranishi, Shozo; "Absorption Enhancers" (1990) Crit. Rev. Ther. Drug Carrier Sys., 7:1–33.

Nielsen, Dorte et al.: "P–Glycoprotein as Multidrug Transporter: A Critical Review of Current Multidrug Resistant Cell Lines" (1992) Biochim. Biophys. Acta. 1139:169–183.

Pearce et al., "Essential Features of the P–Glycoprotein Pharmacophore as Defined by a Series of Reserpine Analogs That Modulate Multidrug Resistance" (1989) Proc. Natl. Acad. Sci., 86:5128–5132.

Peters, W.H. et al., "Expression of Drug–Metabolizing Enzymes and p–170 Glycoprotein in Colorectal Carcinoma and Normal Mucosa", Gastroenterology 103:448–455, 1992.

Pichard et al., "Cyclosporine A Drug Interactions: Screening for Inducers and Inhibitors of Cytochrome P–450 (Cyclosporine A Oxidase) in Primary Cultures of Human Hepatocytes and in Liver Microsomes" (1990) Drug Metab. Dipos. 18:595–606.

Pichard, L., et al., Effect of Corticosteroids on the Expression of Cytochromes P450 and on Cyclosporin A Oxidase Activity in primary Cultures of Human Hepatocytes, Molecular Pharmacology, 41(6): 1047–1055, 1992.

Sands, M., et al., "Interactions of Cyclosporine with Antimicrobial Agents", Reviews of Infectious Diseases, 11:(5)691–697, Sep.–Oct. 1989.

Schmiedlin–Ren, Phyllissa et al.; "Cultured Adult Rat Jejunal Explants as a Model for Studying Regulation of CYP3A" (1993) Biochem. Pharmacol. 46:905–918.

Somberg et al.; "The Clinical Implications of First–Pass Metabolism: Treatment Strategies for the 1990's" (1993) J. clin. Pharmacol. 33:670–673.

Sridhar, T. J., et al., "Influence of Concomitant Medication on Cyclosporine Dosage and Blood Concentrations in Renal Allograft Recipients", Clinical Transplantation, 6(2)134–138, Apr. 1992.

Tam, Yun K.; "Individual Variation in First–Pass Metabolism" (1993) Clin. Pharmacokinet. 25:300–328.

Thierry et al.; "Modulation of Doxorubicin Resistance in Multidrug–Resistant Cell by Liposomes" (1993) FASEB J. 6:572–579.

van Hoogdalem et al.; "Intestinal Drug Absorbtion Enhancement: An Overview" (1989) Pharmacol. Ther. 44:407–443.

Warren et al.; "Increased Accumulation of Drugs in Multidrug–Resistant Cell Induced by Liposomes" (1992) Cancer Research 52:3241–3245.

Watkins et al.: "Identification of Glucocortaiciod–Inducible Cytochromes P–450 in the Intestinal Mucosa of Rats and Man" (1987) J. Clin. Invest. 80:1029–1036.

Watkins, Paul B.; "The Role of Cytochromes P–450 in Cyclosporine Metabolism" (1990) J. Am. Acad. Dermacol. 23:1301–1309.

Watkins et al.; "Erythromycin Breath Test as an Assay of Glucocorticoid–Inducible Liver Cytochromes P–450" (1989) J. Clin. Invest. 83:688–697.

Watkins, Paul B., "Drug Metabolism by Cytochromes P450 in the Liver and Small Bowel" (1992) *Gastrointestinal Pharmacology* 21(3):511–527.

West, I.C.; "What Determines the Substrate Specificity of the Multi–Drug Resistance Pump?" (1990) *TIBS* 15:42–46.

Wrighton et al., "Demonstration in Multiple Species of Inducible Hepatic Cytochromes P–450 and Their mRNAs Related to the Glucorcorticoid–Inducible Cytochrome P–450 of the Rat", Molecular Pharmacology, 28:312–321 (1985).

Wrighton et al.; "Studies on the Expression of Metabolic Capabilities of Human Liver Cytochrome P450IIIA5 (HLp3)" (1990) Molec. Pharmacol. 37:207–213.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorbtion and Metabolism" (1993) Pharm. Res. 10:abstract ppdm8185.

Yee et al., "Pharmacokinetic Drug Interactions with Cyclosporin (Part I)", Clinical Pharmacokinetics, 19(4):319–322, 1990.

Zamora et al.; "Physical–Chemical Properties Shared by Compounds that Modulate Multidrug Resistance in Human Leukemic Cells" (1988) Molec. Pharmacol. 33:454–462.

Keller, et al., "Pharmacologic Interactions Between the Resistance–Modifying Cyclosporine SDZ PSC 833 and Etoposide (VP 16–213) Enhance In Vivo Cytostatic Activity and Toxicity", Int. J. Cancer, 51:433–438 1992.

Qian and Beck, "Binding of an Optimally Pure Photoaffinity Analogue of Verapamil, LU–49888, to P–Glycoprotein from Multidrug–resistant Human Leukemic Cell Lines", Cancer Research, 50:1132–1137 1990.

Burt et al., "Coinduction of MDR–1 Multidrug Resistance and Cytochrome P–450 Genes in Rat Liver by Xenobiotics," *J. Nat'l. Cancer Inst.*, vol. 80:1383–6 (1988).

Kolars et al., "P–450 III Metabolizes Cyclosporin A in Intestinal Mucosa; Observations in a Novel Rat Model," *Clin. Res.*, vol. 37:933A (1989).

Lucey et al., "Cyclosporin Toxicity at Therapeutic Blood Levels and Cytochrome P–450 IIIA," *The Lancet*, vol. 335:11–15 (1990).

Sawchuk et al., "Absorption of Cyclosporin From Rabbit Small Intestine In Situ," *J. Pharm. Sci*, vol. 75:1151–56 (1986).

P.G. Stecher et al. The Merck Index, Eighth Edition, 1968. Rahway, NJ: Merck & Co., Inc. pp. 416 and 862.

METHOD FOR INCREASING BIOAVAILABILITY OF ORALLY ADMINISTERED PHARMACEUTICAL COMPOUNDS

CROSS REFERENCE TO RELATED APPLICATIONS

This application is a Division of U.S. application Ser. No. 08/190,288, filed Feb. 2, 1994, now U.S. Pat. No. 5,567,592.

TECHNICAL FIELD

This invention is directed to the field of pharmacology and particularly to the formulation of pharmaceutical compositions for increased bioavailability.

BACKGROUND

Bioavailability

Pharmacokinetics is the study of the fate of pharmaceuticals from the time they are ingested until they are eliminated from the body. The sequence of events for an oral composition includes absorption through the various mucosal surfaces, distribution via the blood stream to various tissues, biotransformation in the liver and other tissues, action at the target site, and elimination of drug or metabolites in urine or bile.

Bioavailability of a drug (pharmaceutical composition) following oral dosing is a critical pharmacokinetic determinant which can be approximated by the following formula:

$$F_{oral} = F_{ABS} \times F_G \times F_H$$

$F_{oral}$ is oral bioavailability fraction, which is the fraction of the oral dose that reaches the circulation in an active, unchanged form. $F_{oral}$ is less than 100% of the active ingredient in the oral dose for three reasons: drug is not absorbed through the GI tract and is eliminated in the feces; drug is biotransformed by the cells of the intestine (to an inactive metabolite); or drug is eliminated by the cells of the liver, either by biotransformation and/or by transport into the bile. Thus, oral bioavailability is the product of the fraction of the oral dose that is absorbed ($F_{ABS}$), the fraction of the absorbed dose that successfully reaches the blood side of the gastrointestinal tract ($F_G$), and the fraction of the drug in the GI blood supply that reaches the heart side of the liver ($F_H$). Previous drug formulations have attempted to increase drug efficacy by increasing drug absorption. For example, methods have been used to increase drug absorption using liposomes as carriers and designing more lipophilic drugs. These methods can increase drug absorption; however, they fail to address other ways of increasing drug bioavailability.

Liver Biotransformation and Biliary Secretion

The liver affects drug bioavailability. All blood from the gastrointestinal tract passes through the liver before going elsewhere in the body in all mammals, including humans. Due to its location, liver transformation of orally dosed drugs has a substantial "first-pass effect" on drug bioavailability that was thought to exceed effects in the gut, as discussed by Yun K. Tam in "Individual Variation in First-Pass Metabolism," *Clin. Pharmacokinetics* 25:300–328 (1993):

> Enzyme activity in the small intestine is lower than in the liver. In humans, the liver to intestine cytochrome P450 ratio has been reported as ≈20, suggesting that the contribution of intestinal phase I biotransformation to the overall metabolism of a drug is unlikely to be important. (op. cit. 303)

Elimination of active drug by the liver occurs by one or both of two general pathways, namely biotransformation of the drug and excretion of the drug into the bile. Biotransformation reactions have been classified into two broadly defined phases. Phase I biotransformation often utilizes reactions catalyzed by the cytochrome P450 enzymes, which are manifold and active in the liver and transform many chemically diverse drugs. A second biotransformation phase can add a hydrophilic group, such as glutathione, glucuronic acid or sulfate, to increase water solubility and speed elimination through the kidneys.

Hepatocytes have contact with many types of blood and other fluid-transport vessels, such as the portal vein (nutrient and drug-rich blood from the gut), the hepatic arteries (oxygenated blood direct from the heart), the hepatic veins (efflux), lymphatics (lipids and lymphocytes), and bile ducts. The biliary ducts converge into the gall bladder and common bile duct that excretes bile into the upper intestine, aiding digestion. Bile also contains a variety of excretory products including hydrophobic drugs and drug metabolites.

Traditional solubility rate limiting approaches to increasing drug efficacy have focused on increasing solubility and membrane permeability. Where metabolism-based approaches have been considered, they have focused on biotransformation in liver. Although methods exist that affect biotransformation in the liver, these methods are inadequate because they affect general liver metabolism and can produce broad non-specific systemic effects.

Cytochromes

Most biotransformation is performed by enzymes called "mixed function oxidases" containing cytochromes, molecules with iron-containing rings, that help reduce oxygen to water. The cytochrome-containing enzymes that transform drugs use radical oxygen. When oxygen is reduced to its reactive radical form, it reacts immediately with the drug at the oxygen reduction site.

Most research on cytochromes involved in drug biotransformation focuses on inter-individual differences in cytochrome activity because such differences appear to be the dominant mechanism for differences in elimination of pharmaceuticals between individuals. Large inter-individual differences observed in the effects of drugs are at least in part determined by the variation of the expression and catalytic activity of the cytochromes P450.

The sources of the inter-individual variation in the catalytic activity of the cytochromes P450 can be divided into four general categories. The first is the influence of genetics on the expression of the cytochromes P450. Significant inter-individual variability can occur for each of the cytochromes P450. Genetic polymorphisms have been well characterized for the two cytochromes P450 responsible for debrisoquine/sparteine metabolism (CYP2D6; cytochrome families are defined below) and (S)-mephenytoin 4'-hydroxylation (possibly CYP2C19). The second source of inter-individual differences is that several of the human cytochromes P450 are inducible. That is, the content as well as the catalytic activity of these cytochromes P450 is increased by exposure of an individual to particular classes of drugs, endogenous compounds, and environmental agents. Thirdly, the activity of the cytochromes P450 can be inhibited or the cytochromes P450 can be inactivated by drugs and environmental compounds. This includes competitive inhibition between substrates of the same cytochrome P450, inhibition by agents that bind sites on the cytochrome P450 other than the active site, and suicidal inactivation of the cytochrome P450 by reactive intermediates formed during the metabolism of an agent. Another source of inter-individual differences is host factors. These factors include disease states, diet, and hormonal influences. Inter-individual differences in the level of expression and catalytic activity of the various cytochromes P450 can result in an altered response to a drug (individuals can be hypo- or hyper-responsive), a toxic response to unusual levels of a drug or metabolite, and individual sensitivity to chemical carcinogens.

Multiple Drug Resistance

Cancer cells that become resistant to one chemotherapeutic drug often become resistant to an entire group of chemotherapeutic drugs. This phenomenon is usually called multiple drug resistance (MDR).

Many patients on chemotherapy initially have striking remissions but later relapse and die from cancer that exhibits resistance to a wide array of structurally unrelated antineoplastic agents. The MDR phenomenon includes cross-resistance among the anthracyclines, the epipodophyllotoxins, the vinca alkaloids, taxol, and other compounds. A number of drugs are able to reverse MDR, including calcium channel blockers, phenothiazines, quinidine, antimalarial agents, antiestrogenic and other steroids, and cyclosporine. Liposome therapy also reverses MDR, with or without a drug on board.

In vitro studies in the past indicate that this form of resistance is associated with amplification or over-expression of the mdr-1 gene in tumors. The mdr-1 gene codes for the expression of a cell surface protein, P-glycoprotein (P-gp), a transmembrane protein which acts as an energy-dependent efflux pump that transports drugs associated with MDR out of the tumor cell before cytotoxic effects occur. ATP hydrolysis on the cytoplasmic face of P-gp is required for export of hydrophobic compounds from a tumor cell.

Normal mdr-1 expression occurs in secretory epithelial cells of the liver, pancreas, small intestine, colon, and kidney; endothelial capillary cells of the brain and testis; placental trophoblasts; and the adrenal gland. In the liver, P-gp is localized on the biliary domain of the hepatocyte membrane. In the small intestine and colon, P-gp is present on the luminal side of epithelial cells. P-gp transports dietary toxins back into the lumen and therefore helps prevent the toxins from being absorbed into the portal circulation.

Clinical studies have also previously shown that pharmaceuticals that are effective in eliminating MDR of tumor cells in vitro (apparently by inhibition of P-gp) restore chemotherapeutic cytotoxicity in vivo. Studies with small numbers of patients suggest that the addition of verapamil, diltiazem, quinine, trifluoperazine, or cyclosporine to chemotherapeutic regimens has the potential to reverse MDR.

Absorption By The Gut

Absorption across epithelia, in particular intestinal epithelia, also affects drug bioavailability. The intestine lumen presents a convoluted surface that increases the surface area of the intestine to facilitate absorption of both nutrients and drugs. The membrane of the enterocyte contains many transport proteins that actively carry nutrients from the lumen of the gut into the interior of the enterocytes. Many molecules, including many drugs, passively diffuse or are actively transported through the membrane and into the cytoplasm. Most nutrients and drugs pass through the enterocyte and eventually diffuse into the capillary net on route to the portal circulation system and the liver.

The intestine can also pump drugs out of the intestine and back into the lumen. The ability of the intestine to pump drugs out of the tissue has been thought to be important in protection against potentially damaging hydrophobic cations and toxins and for protection against small intestine cancer. No drugs or formulations have been designed to reduce pumping of drugs back into the intestine to increase drug bioavailability prior to the present invention.

Relevant Literature

Back, D. J. and M. L. Orme. "Pharmacokinetic drug interactions with oral contraceptives." *Clin Pharmacokinet* 18 (6 1990): 472–84.

Back, D. J. and S. M. Rogers. "Review: first-pass metabolism by the gastrointestinal mucosa." *Aliment Pharmacol Ther* 1 (5 1987): 339–57.

Benet, L. Z. and R. L. Williams. "Appendix II: Design and optimization of dosage regimes; pharmacokinetic data." In *Goodman and Gilman's The Pharmacological Basis of Therapeutics*, eds. Alfred Gilman, Theodore W. Rail, Alan S. Nies, and Palmer Taylor, Eighth ed., New York: Pergamon Press, 1990.

Callaghan, R. and J. R. Riordan. "Synthetic and natural opiates interact with P-glycoprotein in multidrug-resistant cells." *J. Biol Chem* 268 (21 1993): 16059–64.

Clynes, M. "Cellular models for multiple drug resistance in cancer." *In Vitro Cell Dev Biol* 3 (1 1993): 171–9.

Endicott, J. A. and V. Ling. "The biochemistry of P-glycoprotein-mediated multidrug resistance." *Annu Rev Biochem* 58 (71 1989): 137–71.

Fahr, A. "Cyclosporin clinical pharmacokinetics." *Clin Pharmacokinetic* 24 (6 1993): 472–95.

Fairchild, C. R. and K. H. Cowan. "Keynote address: multidrug resistance: a pleiotropic response to cytoxic drugs." *Int J Radiat Oncol Biol Phys* 20 (2 1991): 361–7.

Fasco, M. J., J. B. Silkworth, D. A. Dunbar, and L. S. Kaminsky. "Rat small intestinal cytochromes P450 probed by warfarin metabolism." *Mol Pharmacol* 43 (2 1993): 226–33.

Fojo, A. T. "Multidrug resistance." *Adv Intern Med* 36 (218 1991): 195–218.

Gatmaitan, Z. C. and I. M. Arias. "Structure and function of P-glycoprotein in normal liver and small intestine." *Adv Pharmacol* 24 (97 1993): 77–97.

Gilman, A. G., T. W. Rall, A. S. Nies, and P. Taylor. *Goodman and Gilman's The Pharmacological Basis of Therapeutics*. Eighth ed., New York: Pergamon Press, 1990.

Gomez, D., M. Hebert, and L. Z. Benet. "The effect of ketoconazole on the intestinal metabolism and bioavailability of cyclosporine" *Clin Pharmacol Ther* 55 (2 1994): in press.

Greenblatt, D. J. "Presystemic extraction: mechanisms and consequences." *J Clin Pharmacol* 33 (7 1993): 650–6.

Hait, W. N., J. F. Gesmonde, J. R. Murren, J. M. Yang, H. X. Chen, and M. Reiss, "Terfenadine (Seldane): a new drug for restoring sensitivity to multidrug resistant cancer cells." *Biochem Pharmacol* 45 (2 1993): 401–6.

Hebert, M. F., J. P. Roberts, T. Prueksaritanont, and L. Z. Benet. "Bioavailability of cyclosporine with concomitant rifampin administration is markedly less than predicted by hepatic enzyme induction." *Clin Pharmacol Ther* 52 (5 1992): 453–7.

Hsing, S., Z. Gatmaitan, and J. M. Arias. "The function of Gp170, the multidrug-resistance gene product, in the brush border of rat intestinal mucosa." *Gastroenterology* 102 (3 1992): 879–85.

Hunter, J., B. H. Hirst, and N. L. Simmons. "Drug absorption limited by P-glycoprotein-mediated secretory drug transport in human intestinal epithelial Caco-2 cell layers." *Pharm Res* 10 (5 1993): 743–9.

Jancis, E. M., R. Carbone, K. J. Loechner, and P. S. Dannies. "Estradiol induction of rhodamine 123 efflux and the multidrug resistance pump in rat pituitary tumor cells." *Mol Pharmacol* 43 (1 1993): 51–6.

Kaminsky, L. S. and M. J. Fasco. "Small intestinal cytochromes P450." *Crit Rev Toxicol* 21 (6 1991): 407–22.

Kolars, J. C., P. Schmiedlin-Ren, J. D. Schuetz, C. Fang, and P. B. Watkins. "Identification of rifampin-inducible P450IIIA4 (CYP3A4) in human small bowel enterocytes." *Clin Invest* 90 (5 1992a): 1871–8.

Kolars, J. C., P. Schmiedlin-Ren, W. O. 3rd Dobbins, J. Schuetz, S. A. Wrighton, and P. B. Watkins. "Heterogeneity of cytochrome P450IIIA expression in rat gut epithelia." *Gastroenterology* 102 (4 Pt 1 1992b): 1186–98.

Kolars, J. C., P. L. Stetson, B. D. Rush, M. J. Ruwart, R. P. Schmiedlin-Ren, E. A. Duell, J. J. Voorhees, and P. B. Watkins. "Cyclosporine metabolism by P450IIIA in rat enterocytes—another determinant of oral bioavailability?" *Transplantation* 53 (3 1992c): 596–602.

Komori, M., T. Hashizume, H. Ohi, T. Miura, M. Kitada, K. Nagashima, and T. Kamataki. "Cytochrome P-450 in human liver microsomes: high-performance liquid chromatographic isolation of three forms and their characterization." *J. Biochem* 104 (6 1988): 912–6.

Kralovanszky, J., F. Harrington, A. Greenwell, and R. Melnick. "Isolation of viable intestinal epithelial cells and their use for in vitro toxicity studies." *In Vivo* 4 (3 1990): 201–4.

Kronbach, T. V., Fischer, and U. A. Meyer. "Cyclosporine metabolism in human liver: identification of a cytochrome P-450III gene family as the major cyclosporine-metabolizing enzyme explains interactions of cyclosporine with other drugs." *Clin Pharmacol Ther* 43 (6 1988): 630–5.

Kronbach, T. D. Mathys, M. Umeno, F. J. Gonzalez, and U. A. Meyer. "Oxidation of midazolam and triazolam by human liver cytochrome P450IIIA4." *Mol Pharmacol* 36 (1 1989): 89–96.

Lalka, D., R. K. Griffith, and C. L. Cronenberger. "The hepatic first-pass metabolism of problematic drugs." *J Clin Pharmacol* 33 (7 1993): 657–69.

Ludescher, C., Gattringer, J. Drach, J. Hofmann, and H. Grunicke. "Rapid functional assay for the detection of multidrug-resistant cells using the fluorescent dye rhodamine 123 [letter; comment]." *Blood* 78 (5 1991): 1385–7.

Ludescher, C., J. Thaler, D. Drach, J. Drach, M. Spitaler, C. Gattringer, H. Huber, and J. Hofmann. "Detection of activity of P-glycoprotein in human tumor samples using rhodamine 123." *Br J Haematol* 82 (1 1992): 161–8.

Lum, B. L., G. A. Fisher, N. A. Brophy, A. M. Yahanda, K. M. Adler, S. Kaubisch, J. Halsey, and B. I. Sikie. "Clinical trials of modulation of multidrug resistance. Pharmacokinetic and pharmacodynamic considerations." *Cancer* 72 (11 Suppl 1993a): 3502–14.

Lum, B. L., M. P. Gosland, S. Kaubisch, and B. I. Sikic. "Molecular targets in oncology: implications of the multidrug resistance gene." *Pharmacotherapy* 13 (2 1993): 88–109.

Muranishi, S. "Absorption enhancers." *Crit Rev Ther Drug Carrier Syst* 7 (1 1990): 1–33.

Nielsen, D. and T. Skovsgaard. "P-glycoprotein as multidrug transporter: a critical review of current multidrug resistant cell lines." *Biochim Biophys Acta* 1139 (3 1992): 169–83.

Pearce, H. I., A. R. Safa, N. J. Bach, M. A. Winter, M. C. Cirtain, and W. T. Beck. "Essential features of the P-glycoprotein pharmacophore as defined by a series of reserpine analogs that modulate multidrug resistance." *Proc Natl Acad Sci USA* 86 (13 1989): 5128–32.

Pichard, L., I. Fabre, G. Fabre, J. Domergue, B. Saint Aubert, G. Mourad, and P. Maurel. "Cyclosporine A drug interactions. Screening for inducers and inhibitors of cytochrome P-450 (cyclosporin A oxidase) in primary cultures of human hepatocytes and in liver microsomes." *Drug Metab Dipos* 18 (5 1990): 595–606.

Schmiedlin-Ren, P., P. E. Benedict, W. O. 3rd Dobbins, M. Ghosh, J. C. Kolars, and P. B. Watkins. "Cultured adult rat jejunal explants as a model for studying regulation of CYP3A." *Biochem Pharmacol* 46 (5 1993): 905–18.

Somberg, J., G. Shroff, S. Khosla, and S. Ehrenpreis. "The clinical implications of first-pass metabolism: treatment strategies for the 1990s." *J Clin Pharmacol* 33 (7 1993): 670–3.

Tam, Y. K. "Individual variation in first-pass metabolism." *Clinical Pharmacokinetics* 25 (4 1993): 300–328.

Thierry, A. R., D. Vige, S. S. Coughlin, J. A. Belli, A. Dritschilo, and A. Rahman. "Modulation of doxorubicin resistance in multidrug-resistant cells by liposomes." *FASEB J* (6 1993): 572–9.

van Hoogdalem, E. J., A. G. de Boer, and D. D. Breimer. "Intestinal drug absorption enhancement: an overview." *Pharmacol Ther* 44 (3 1989): 407–43.

Warren, L., J. -C. Jardiller, A. Malarska, and M. -G. Akeli: "Increased accumulation of drugs in multidrug-resistance cells induced by liposomes" *Cancer Research* 52:3241 (1992).

Watkins, P. B. "The role of cytochromes P-450 in cyclosporine metabolism." *J Am Acad Dermatol* 23 (6 Pt 2 1990): 1301–9.

Watkins, P. B. "Drug metabolism by cytochromes P450 in the liver and small bowel." *Gastroenterology Clinics of North America* 21 (3 1992): 511–526.

Watkins, Paul B. "Drug metabolism by cytochromes P450 in the liver and small bowel." *Gastroenterology Clinics of North America* 21 (3 1992): 511–526.

Watkins, P. B., S. A. Murray, L. G. Winkelman, D. M. Heuman, S. A. Wrighton, and P. S. Guzelian. "Erythromycin breath test as an assay of glucocorticoid-inducible liver cytochromes P-450. Studies in rats and patients." *J Clin Invest* 83 (2 1989): 688–97.

Watkins, P. B., S. A. Wrighton, E. G. Schuetz. D. T. Molowa, and P. S. Guzelian. "Identification of glucocorticoid-inducible cytochromes P-450 in the intestinal mucosa of rats and man." *J Clin Invest* 80 (4 1987): 1029–36.

West, I. C. "What determines the substrate specificity of the multi-drug-resistance pump?." *Trends Biochem Sci* 15 (2 1990): 42–6.

Wrighton, S. A., W. R. Brian, M. A. Sari, M. Iwasaki, F. P. Guengerich, J. L. Raucy, D. T. Molowa, and M. Vandenbranden. "Studies on the expression and metabolic capabilities of human liver cytochrome P450IIIA5 (HLp3)." *Mol Pharmacol* 38 (2 1990) 207–13.

Wrighton, S. A., M. Vandenbranden, J. C. Stevens, L. A. Shipley, B. J. Ring, A. E. Rettie, and J. R. Cashman. "In vitro methods for assessing human hepatic drug metabolism: their use in drug development." *Drug Metabolism Reviews* 25 (4 1993): 453–484.

Wu, C. -Y., M. F. Hebert, and L. Z. Benet. "Use of IV and oral drug levels from cyclosporine (CSA) with concomitant rifampin to differentiate gut absorption and metabolism." *Pharm Res* 10 Supp. (1993): S-345.

Zamora, J. M., H. L. Pearce, and W. T. Beck. "Physical-chemical properties shared by compounds that modulate multidrug resistance in human leukemic cells." *Mol Pharmacol* 33 (4 1988): 454–62.

SUMMARY OF THE INVENTION

The invention is concerned with optimization of drug bioavailability. The invention maximizes drug bioavailability by increasing net drug absorption or decreasing drug biotransformation in the gut by using either cytochrome P450 drug metabolism inhibitors or P-glycoprotein (P-gp) drug transport inhibitors, both of which are called "bioenhancers" for the purposes of this invention.

An important object of the invention is inhibiting enzymes of the cytochrome P450 3A class (CYP3A) in the gut in preference to other locations, such as the liver, which was previously thought to be the primary site of drug metabolism. Another object of the invention is to inhibit P-gp-controlled back transport to increase the net transport of drugs through the enterocyte layer, causing an increase in the bioavailability of the drug, since the protein P-gp pumps drugs that have been transported into the cytoplasm of the enterocytes back into the lumen of the gut.

The invention is carried out by coadministration of one or more bioenhancers with a drug or drugs to increase drug bioavailability. The compositions and methods of the present invention can be used to increase drug efficacy in humans and in other mammals. Although veterinary use is specifically contemplated, the primary use will be in human treatment. Administration schemes include, but are not limited to, use of oral and topical formulations in humans and use of similar formulations for livestock.

One specific object of the present invention is to reduce inter-individual variability of the systemic concentrations of the compound, as well as intra-individual variability of the systemic concentrations of the pharmaceutical compound being administered.

DESCRIPTION OF SPECIFIC EMBODIMENTS

Bioenhancers Increase Drug Bioavailability

Figure 1:
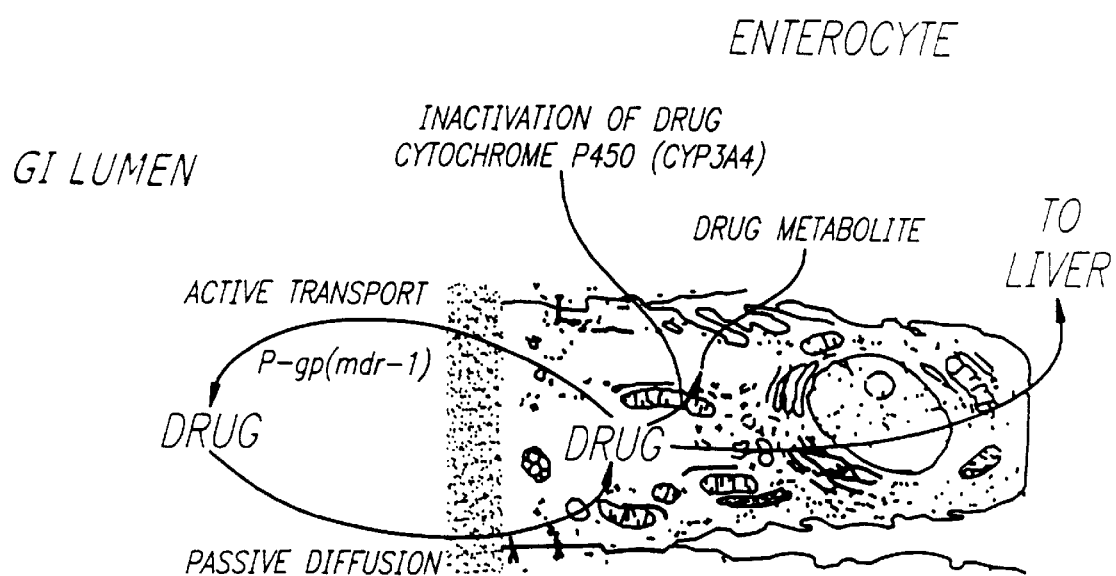
FIG. 1 is a diagram of enterocyte cytochrome P450 3A drug metabolism and P-glycoprotein drug transport mechanisms that lead to decreased drug bioavailability.
Figure 2:
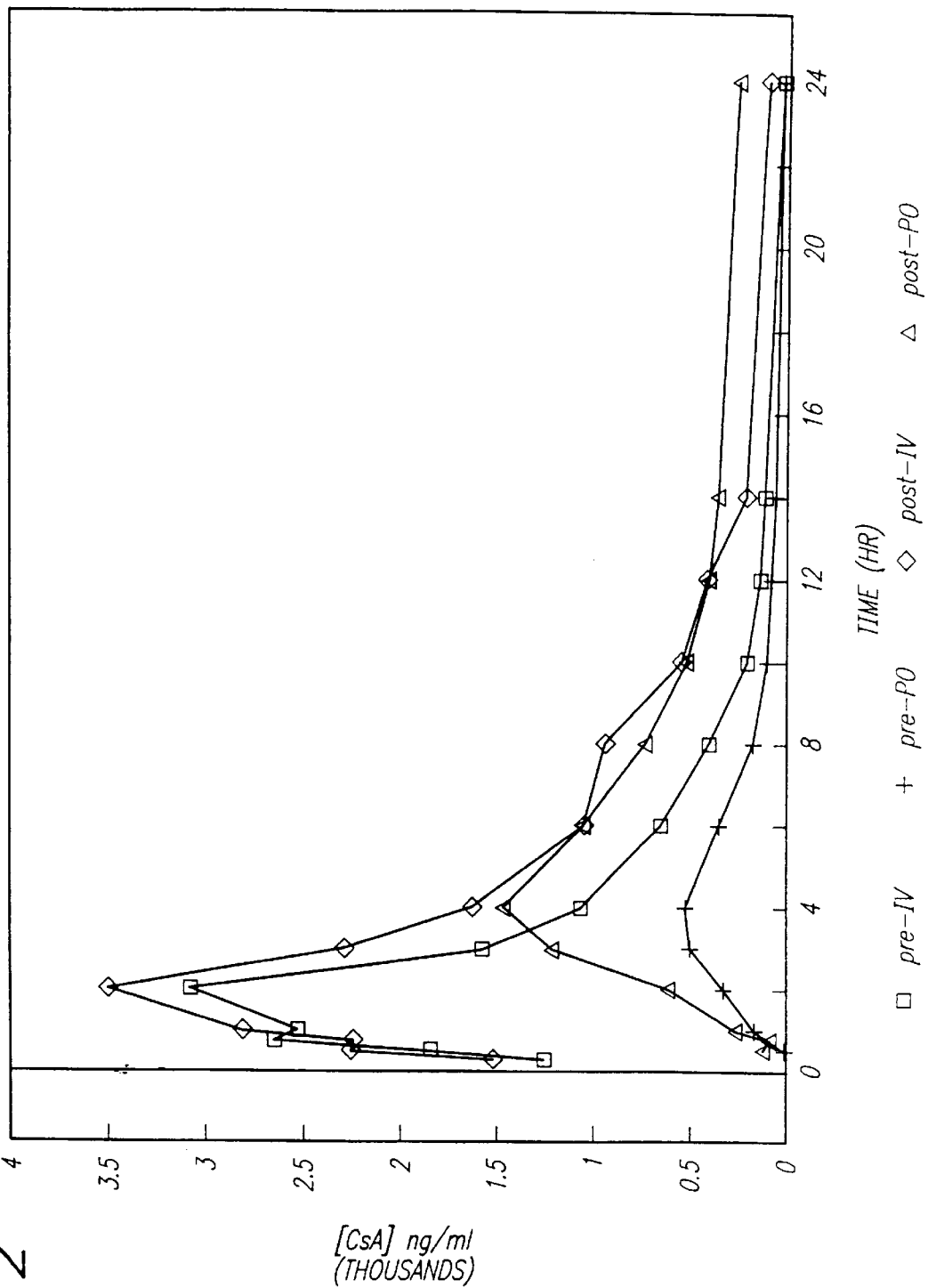
FIG. 2 is a graph showing the increase in cyclosporine (CYA) bioavailability caused by co-administration of ketoconazole (KC), a bioenhancer. Pre-IV indicates administration of CYA prior to IV administration of KC. Post-IV indicates administration of CYA after IV administration of KC. Pre-PO indicates oral administration of CYA prior to oral administration of KC. Post-PO indicates oral administration of CYA after oral administration of KC. The data illustrate an increase in integrated systemic drug concentrations over time due to the addition of a bioenhancer, as indicated by the increase in the area under the curve from pre-PO to post-PO which is markedly greater than the enhancement seen for the increase in the area under the curve (AUC) from pre-IV to post-IV.

The present invention is based on a new discovery of various factors affecting drug bioavailability. "Drug bioavailability" is defined as the total amount of drug systemically available over time. The present invention increases drug bioavailability by inhibiting drug biotransformation in the gut and/or by inhibiting active transport systems in the gut which decrease the net transport of drugs across gut epithelia. In either case the composition responsible for increased drug bioavailability is called a bioenhancer in this specification. It has been discovered that, in contrast to previous teachings about the primacy of liver metabolism, the gut is the primary location of drug transformation for many drugs, if not the majority of drugs dosed orally. Thus, bioenhancers specifically targeted to the gut provide a number of advantages, as described in detail below.

In general, the present invention provides a method for increasing the bioavailability of an orally administered pharmaceutical compound (particularly one which is hydrophobic), which comprises orally administering the pharmaceutical compound to a mammal in need of treatment concurrently with a bioenhancer comprising an inhibitor of a member of the cytochrome P450 3A enzyme family or an inhibitor of P-glycoprotein-mediated membrane transport (or both), the bioenhancer being present in sufficient amount to provide integrated systemic concentrations over time of the compound greater than the integrated systemic concentrations over time of the compound in the absence of the composition. Changes in the integrated systemic concentrations over time are indicated by the area under the curve (AUC) defined below. In preferred embodiments side effects are reduced by providing a bioenhancer that is active only (or primarily) in the gut, either because of its structure or because of deliberately selected concentration effects.

Bioavailability Measurements

The increase in drug bioavailability attributable to administration of the bioenhancer can be determined by measuring total systemic drug concentrations over time after coadministration of a drug and a bioenhancer and after administration of only the drug. The increase in drug bioavailability is defined as an increase in the Area Under the Curve (AUC). AUC is the integrated measure of systemic drug concentrations over time in units of mass-time/volume. The AUC from time zero (the time of dosing) to time infinity (when no drug remains in the body) following the administration of a drug dose is a measure of the exposure of the patient to the drug. When efficacy of the bioenhancer is being measured, the amount and form of active drug administered should be the same in both the coadministration of drug and bioenhancer and the administration of the drug alone. For instance, administration of 10 mg of drug alone may result in total systemic drug delivered over time (as measured by AUC) of 500 μg-hr/ml. In coadministration (i.e., in the presence of the bioenhancer) the systemic drug AUC will increase to 700 μg-hr/ml. However, if significantly increased drug bioavailability in the presence of the bioenhancer is anticipated, drug doses may need to be reduced for safety. Systemic drug concentrations are measured using standard in vitro or in vivo drug measurement techniques. "Systemic drug concentration" refers to a drug concentration in a mammal's bodily fluids, such as serum, plasma or blood; the term also includes drug concentrations in tissues bathed by the systemic fluids, including the skin. Systemic drug concentration does not refer to digestive fluids. The increase in total systemic drug concentrations is one way of defining an increase of drug bioavailability due to coadministration of bioenhancer and drug. For drugs excreted unmetabolized in the urine, an increased amount of unchanged drug in the urine will reflect the increase in systemic concentrations.

Characteristics of Drugs Used With Bioenhancers

The word "drug" as used herein is defined as a chemical capable of administration to an organism which modifies or alters the organism's physiology. More preferably the word "drug" as used herein is defined as any substance intended for use in the treatment or prevention of disease. Drug includes synthetic and naturally occurring toxins and bio-affecting substances as well as recognized pharmaceuticals, such as those listed in "The Physicians Desk Reference," 47th edition, 1993, pages 101–321; "Goodman and Gilman's The Pharmacological Basis of Therapeutics" 8th Edition (1990), pages 84–1614 and 1655–1715; and "The United States Pharmacopeia, The National Formulary", USP XXII NF XVII (1990), the compounds of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water. Preferably, a hydrophobic drug is defined as a drug more soluble in octanol than in water.

Increased Drug Bioavailability by Inhibition of Cytochrome P450

Phase I Biotransformation

Reduction of enterocyte cytochromes P450 participation in drug biotransformation is one objective of the present invention. The major enzymes involved in drug metabolism are present in the endoplasmic reticulum of many types of cells but are at the highest concentration in hepatocytes. Traditionally, enterocyte biotransformation was considered of minor importance in biotransformation compared to the liver. Many compounds inhibit cytochrome P450. These include, but are not limited to, ketoconazole, troleandomycin, gestodene, flavones such as quercetin and naringenin, erythromycin, ethynyl estradiol, and prednisolone. The first goal of the invention is to use cytochrome P450 inhibitors to inhibit drug cytochrome P450 biotransformation in the gut to increase drug bioavailability.

Types Of Cytochromes And Tissue Location

The cytochromes P450 are a superfamily of hemoproteins. They represent the terminal oxidases of the mixed function oxidase system. The cytochrome P450 gene superfamily is composed of at least 207 genes that have been named based on the evolutionary relationships of the cytochromes P450. For this nomenclature system, the sequences of all of the cytochrome P450 genes are compared, and those cytochromes P450 that share at least 40% identity are defined as a family (designated by CYP followed by a Roman or Arabic numeral, e.g. CYP3), further divided into subfamilies (designated by a capital letter, e.g. CYP3A), which are comprised of those forms that are at least 55% related by their deduced amino acid sequences. Finally, the gene for each individual form of cytochrome P450 is assigned an Arabic number (e.g. CYP3A4).

Three cytochrome P450 gene families (CYP1, CYP2 and CYP3) appear to be responsible for most drug metabolism. At least 15 cytochromes P450 have been characterized to varying degrees in the human liver. At concentrations of the substrates found under physiologic conditions, enzyme kinetics often favor a single form of cytochrome P450 as the primary catalyst of the metabolism of a particular drug or other enzyme substrate.

The CYP3 gene family encoding cytochromes P450 of type 3 is possibly the most important family in human drug metabolism. At least S forms of cytochrome P450 are found in the human 3A subfamily, and these forms are responsible for the metabolism of a large number of structurally diverse drugs. In non-induced individuals 3A may constitute 15% of the P450 enzymes in the liver. In enterocytes, members of the 3A subfamily constitute greater than 70% of the cytochrome-containing enzymes. The first two human 3A subfamily members identified were 3A3 and 3A4. These two cytochromes P450 are so closely related that the majority of studies performed to date have not been able to distinguish their contributions, and thus they are often referred to as 3A3/4. Erythromycin N-demethylation, cyclosporine oxidation, nifedipine oxidation, midazolam hydroxylation, testosterone 6β-hydroxylation, and cortisol 6β-hydroxylation are all in vitro probes of 3A3/4 catalytic activity. The levels of 3A3/4 vary by as much as 60-fold between human liver microsomal samples with the levels of 3A forms approaching 50% of the total cytochrome P450 present in human liver samples from individuals receiving inducers of 3A3/4. The recently studied CYP3A5 may also play a role as important as 3A3/4.

The liver contains many isoforms of cytochrome P450 and can biotransform a large variety of substances. The enterocytes lining the lumen of the intestine also have significant cytochrome P450 activity, and this activity is dominated by a single family of isozymes, 3A, the most important isoforms in drug metabolism.

Increased Drug Efficacy By Reducing CYP3A Drug Biotransformation

Preferred bioenhancers of the invention reduce drug biotransformation in the gut by inhibiting CYP3A activity in gut epithelial cells. Inhibition of CYP3A by bioenhancers in gut epithelia will lead to a total increase in drug bioavailability in the serum. Fewer drug molecules will be metabolized by phase I enzymes in the gut and will not be available for phase II conjugation enzymes. This will lead to increased concentrations of untransformed drug passing from gut into the blood and onto other tissues in the body.

Another object of the invention is to reduce variability of oral bioavailability. Reduction of drug biotransformation or increased drug absorption will decrease variability of oral bioavailability to some degree because the increase in bioavailability will begin to approach the theoretical maximum of 100% oral bioavailability. The increase in oral bioavailability will be generally larger in subjects with lower oral bioavailability. The result is a reduction in inter-individual and intra-individual variation. Addition of bioenhancer will reduce inter-individual and intra-individual variation of systemic concentrations of a drug or compound.

Although the primary objective of the bioenhancer is to inhibit CYP3A drug biotransformation in the gut, some biotransformation may be decreased in other tissues as well if the bioenhancer is absorbed into the blood stream. The decrease in biotransformation by other tissues will also increase drug bioavailability. The advantage of targeting a bioenhancer to the gut, however, is that it allows the use of lower systemic concentrations of bioenhancer compared to inhibitors that target CYP3A in the liver. After oral administration of a bioenhancer, concentrations will be highest at the luminal surface of the gut epithelia, not having been diluted by systemic fluids and the tissues of the body. Luminal concentrations that are greater compared to blood concentrations will permit preferential inhibition of CYP3A in gut instead of the liver. Bioenhancers that preferentially inhibit gut CYP3A will also be a particularly effective means of increasing drug bioavailability while minimizing the effects of greater concentrations of bioenhancers in tissues other than the gut.

A Net Increase in Drug Bioavailability Due to a Decrease in the Activity of CYP3A.

The activity of CYP3A is defined as CYP3A catalyzed production of reaction product from CYP3A substrates. Substrates for CYP3A can be naturally occurring substrates or other components such as those listed in Table 1. In addition, some of the CYP3A inhibitors listed in Table 1 have been identified as substrates, as designated in the table. Most likely many if not all of these inhibitors will be shown to be 3A substrates through further research, although allosteric effects are also possible. The catalytic activities of CYP3A, subject to inhibition, include, but are not limited to, dealkyase, oxidase, and hydrolase activities. In addition to the different catalytic activities of CYP3A, different forms of CYP3A exist with a range in molecular weight (for example, from 51 kD to 54 kD, as shown in Komori et al., *J. Biochem.* 1988, 104:912–16).

TABLE 1

| P450 3A substrates | P450 3A inhibitors |
|---|---|
| Antiarrhythmic | Antidiabetic |
| Amiodarone | Glibenclamide |
| Lidocaine | Tolbutamide |
| Quinidine | Benzodiazepine |
| Antiepileptic | Midazolam* |
| Ethosuximide | Calcium channel blocker |
| Zonisamide | Diltiazem |
| Antidepressant | Felodipine |
| Imipramine | Nicardipine |
| Tianeptine | Nifedipine* |
| Benzodiazepine | Verapamil |
| Clonazepam | Chemotherapeutic |
| Diazepam | Clotrimazole |
| Triazolam | Erythromycin* |
| Chemotherapeutics | Fluconazole |
| Dapsone | Itraconazole |
| Ifosfamide | Josamycin |
| Environmental toxins | Ketoconazole |
| 1.6-dinitropyrene | Miconazole |
| 1-nitropyrene | Midecamycin |
| 6-nitrochrysene | Navelbine* |
| Aflatoxin B1 | Primaquine |
| Benzo(a)pyrene | Triacetylolendomycin* |
| MOCA[1] | Vinblastine* |
| PhIP[2] | Vincristine* |
| Immunosuppressant | Vindesine* |
| Cyclosporine | Flavanoids |
| FK-506 | Benzoflavone |
| Rapamycin | Kaempferol |
| Narcotic | Naringenin |
| Alfentanil | Quercetin |
| Cocaine | Steroid hormone |
| Codeine | Cortisol* |
| Ethylmorphine | Ethinylestradiol* |
| Steroid hormones | Gestodene |
| 17 α-ethynylestradiol | Methylprednisolone |
| Estradiol | Norgestrel |
| Flutamide | Prednisolone |
| Testosterone | Prednisone |
| Miscellaneous | Progesterone* |
| 1-tetrahydrocannabinol | Tamoxifen* |
| Acetaminophen | Thiotestosterone |
| Benzphetamine | Miscellaneous |
| Dextromethorphan | Bromocriptine |
| Digitoxin | DDEP |
| Lovastatin | Dihydroergotamine |
| NOHA[3] | Ergotamine |
| Retinoic acid | |
| Selegiline | |
| Terfenadine | |

*Drugs marked * have also been identified as P450 3A substrates.
[1]MOCA: 4,4'-Methylene-bis(2-Chloroaniline)
[2]PhIP: 2-amino-1-methyl-6-phenylimidazo[4,5-b]pyridine
[3]NOHA: N-omega-hydroxy-L-arginine
[4]DDEP: 3,5-dicarbethoxy-2,6-dimethyl-4-ethyl-1,4-dihydropyridine Some bioenhancers reduce CYP3A drug biotransformation by acting either as an inhibitor of CYP3A activity or as a substrate of CYP3A activity. The bioenhancer acting either as the inhibitor or the substrate of CYP3A can act as a competitive, non-competitive, uncompetitive, mixed or irreversible inhibitor of CYP3A drug biotransformation. Additionally, bioenhancer can have properties of being a ligand for P-gp or cytochrome P450 or a ligand for either proteins. Bioenhancers can also include combinations of compounds of different properties. For example, a first compound can act as a P-gp inhibitor while a second compound acts as a CYP3A inhibitor. Bioenhancer can also be bound to the drug being protected, either by covalent bonding or by ionic or polar attractions. Compounds (or drugs) from a number of classes of compounds can be administered with a bioenhancer or can act as a bioenhancer, for example, but not limited to, the following classes: acetanilides, anilides, aminoquinolines, benzhydryl compounds, benzodiazepines, benzofurans, cannabinoids, cyclic peptides, dibenzazepines, digitalis gylcosides, ergot alkaloids, flavonoids, imidazoles, quinolines, macrolides, naphthalenes, opiates (or morphinans), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and vinca alkaloids. "Compound" as used herein also includes dihydropyridine, nitrogen mustard, and phenylpiperidine.

Selection of Compounds for use as Bioenhancers by Reduction of CYP3A Drug Biotransformation The relative ability of compounds to act as bioenhancers and to increase drug bioavailability can be estimated using in vitro and in vivo drug biotransformation measurements. In vivo measurements of drug bioavailability, such as measuring serum or blood drug concentrations over time, provide the closest measure of total drug systemic availability (bioavailability). In vitro assays of CYP3A metabolism and P-gp-transport, as discussed below, indirectly indicate drug bioavailability because CYP3A drug metabolism and P-gp drug transport affect integrated systemic drug concentrations over time. Generally, the ability of a compound being tested to act as a bioenhancer is demonstrated when the addition of the compound to a drug biotransformation assay decreases CYP3A drug biotransformation. Although even a minimally measured increase is all that is required for a compound to be a bioenhancer, a commercially desirable bioenhancer acting as a CYP3A modulator generally will increase drug bioavailability by at least 10%, preferably by at least 50%, and more preferably by at least 75% of the difference between bioavailability in the presence of the bioenhancer and total availability of the ingested dosage in the absence of the bioenhancer. A sufficient amount of orally administered bioenhancer will provide integrated systemic drug concentrations over time greater than the integrated systemic drug concentrations over time in the absence of bioenhancer.

Compounds that can inhibit enzymes of the P450 3A class can be identified by a variety of bioassays, several of which are set out below.

In vitro CYP3A Assays and Increased Drug Bioavailability

Cell Assays of CYP3A Function and Increased Drug Bioavailability

Cultured cells of either hepatocytes or enterocytes or freshly prepared cells from either liver or gut can be used to determine the ability of a compound to act as a CYP3A inhibitor. Various methods of gut epithelial cell isolation can be used such as the method of Watkins et al., *J. Clin. Invest.* 1985; 80:1029–36. Cultured cells, as described in Schmiedlin-Ren, P. et al., *Biochem. Pharmacol.* 1993; 46:905–918, can also be used. The production of CYP3A metabolites in cells can be measured using high pressure liquid chromatograph (HPLC) methods as described in the following section for microsome assays of CYP3A activity.

Microsome Assays of CYP3A Function and Increased Bioavailability

Microsomes from hepatocytes or enterocytes will be used for CYP3A assays. Microsomes can be prepared from liver using conventional methods as discussed in Kronbach et al., *Clin. Pharmacol. Ther* 1988; 43:630–5. Alternatively, microsomes can be prepared from isolated enterocytes using the method of Watkins et al., *J. Clin. Invest.* 1987; 80:1029–1037. Microsomes from gut epithelial cells can also be prepared using calcium precipitation as described in Bonkovsky, H. L. et al., *Gastroenterology* 1985; 88:458–467. Microsomes can be incubated with drugs and the metabolites monitored as a function of time. In addition the levels of these enzymes in tissue samples can be measured using radioimmunoassays or western blots.

Isolated microsomes will be used to determine bioenhancer inhibition of CYP3A drug biotransformation. Generally, the drug will be a substrate of CYP3A. The addition of the bioenhancer will decrease the ability of CYP3A to catalyze drug metabolism. Bioenhancers identified in this assay will be inhibitors of CYP3A function and diminish substrate catalysis. The production of metabolites can be monitored using high pressure liquid chromatography systems (HPLC) and identified based on retention times. CYP3A activity can also be assayed by colorimetrically measuring erythromycin demethylase activity as the production of formaldehyde as in Wrighton, et al., *Mol. Pharmacol.* 1985; 28:312–321 and Nash, T., *Biochem. J.* 1953; 55:416–421.

Characteristics of Bioenhancers that Reduce CYP3A Drug Metabolism

Bioenhancers that reduce CYP3A drug metabolism will generally be hydrophobic compounds that can pass across cell membranes and reduce CYP3 drug metabolism in the manner previously indicated.

Preferably the bioenhancer(s) will bind CYP3A quickly and inhibit while the drug is passing through the enterocyte. After the bioenhancer diffuses out of the enterocyte, normal CYP3A function will return. Reversible and irreversible inhibitors will both have marked effects on gut drug metabolism following oral dosing. After the bioenhancers reach the heart and are distributed throughout the body the concentrations of the bioenhancers will be diluted on future passes through the liver. Concentrations of bioenhancer in the gut lumen are preferably selected to be effective on gut CYP3A metabolism but, due to dilution, to be less active in other tissues.

The amount of bioenhancer used for oral administration can be selected to achieve small intestine luminal concentrations of at least 1/10 of the $K_i$ for CYP3A inhibition of drug metabolism or an amount sufficient to increase systemic drug concentration levels, whichever is less. Alternatively, the amount of an inhibitor of cytochrome P450 3A enzyme that will be used in a formulation can be calculated by various assays that are described in detail below. For example, one such assay measures the conversion of cyclosporine to hydroxylated products in an assay system containing 100 $\mu$g human liver microsomes, 25 $\mu$M cyclosporine, and an NADPH regenerating system in 100 $\mu$l of 0.1 M sodium phosphate buffer, pH 7.4. The initial inhibitor amount is selected to provide concentrations in the lumen of the small intestine equal or greater than concentrations that reduce the rate of conversion determined by this assay, preferably a rate reduction of at least 10%. While the actual dose of inhibitor in a clinical formulation might be optimized from this initial dosage depending on the results of a clinical trial, the assay as described is sufficient to establish a utilitarian dosage level.

Increased Drug Bioavailability by Inhibition of P-glycoprotein (P-gp)

Increased Drug Absorption By Decreasing P-gp Drug Transport

One embodiment of the present invention further increases bioavailability by increasing net drug absorption in the gut. Traditionally, drug absorption by the gut was considered to be the result of a passive diffusion process. Drugs were thought to diffuse into the gut based on the concentration gradient across the gut epithelial cells. Net drug transport across the gut, however, is the net result of drug influx and back flux, some of which is active drug transport. Drug influx is the flux from lumen to blood. Drug back flux is from blood or epithelium cytoplasm into the lumen. The invention reduces P-gp active drug transport across the luminal membrane to prevent return of drugs absorbed into the cytoplasm of the enterocytes back to the lumen of the gut.

Generally, the invention will reduce P-gp active drug transport in order to increase the net transport of drugs across the gut epithelium. An epithelium exists in a number of different tissue types including, but not limited to, the epithelia of the skin, liver, kidneys, adrenals, intestine, and colon. Such epithelia would be affected by systemic administration of P-gp inhibitors. However, the major effects of the invention will be limited to the gut because of concentration effects resulting from oral delivery.

In embodiments of the invention where the bioenhancer comprises an inhibitor of P-glycoprotein-mediated membrane transport the structure of the bioenhancer can vary widely as long as P-gp-mediated transport is reduced. A number of different molecules are known to inhibit this transport system, and a number of examples are given below. However, whether a given compound acts as an inhibitor is best determined by activity assays, such as those described below, rather than by reliance on the structure of the molecule.

Because of the many different structures that can act as inhibitors, the oral dosage of inhibitor to be present in the formulation (or elsewise as described below) is best determined empirically, as the dosage will depend on the affinity of the inhibitor for P-gp relative to the drug's affinity for P-gp. There are a number of assays available that allow the desired dosage to be readily determined without requiring clinical trials. While the actual dosage of inhibitor in a clinical formulation might be optimized from this initial dosage depending on results of a clinical trial, the assay as described is sufficient to establish a utilitarian dosage level.

Selection of Compounds for Use as Bioenhancers by Reduction of P-gp Drug Transport/Activity The relative ability of compounds to act as bioenhancers and to increase drug bioavailability can be estimated using in vitro and in vivo drug transport measurements. Compounds acting as a bioenhancer will cause a net increase in drug diffusion resulting from a decrease in active P-gp drug transport activity. The activity of P-gp is defined either as ATP dependent membrane transport of a drug or as drug-dependent ATP hydrolysis. P-gp activity or drug flux can be measured using in vitro or in vivo measurements such as, but not limited to, voltage sensitive electrodes or dyes, or chemical sensitive electrodes or dyes, substrate or product analysis, electron microscopy or coupled assays. The form of P-gp used in the assay can vary in molecular weight depending on the species, isoform, amount of glycosylation, and molecular weight assay method. Typically, the molecular weight of the P-gp will be approximately 170 kilodaltons.

The bioenhancer, acting as either the inhibitor or the substrate of P-gp, acts as a competitive, uncompetitive, non-competitive, mixed or irreversible inhibitor of P-gp drug transport. The bioenhancer, as an inhibitor or substrate of P-gp, can be either a transportable or non-transportable ligand of P-gp. The bioenhancer can bind to the P-gp on its lumen accessible surface, cytoplasmic accessible surface or membrane spanning region. The bioenhancer can be a ligand of P-gp, a ligand of cytochrome P450, or a ligand of both, or any combination of the three types of ligands. For example a bioenhancer can comprise a ligand of P-gp plus a ligand of cytochrome P450 or a ligand of P-gp plus a ligand that binds to both P-gp and cytochrome P450.

Characteristics of bioenhancers that reduce P-gp drug transport

Some of the structural features that have been found for inhibitors of P-glycoprotein-mediated membrane transport include hydrophobic character of the molecule, especially those comprising two co-planar aromatic rings, a positively charged nitrogen group, or a carbonyl group. However, these characteristics are not essential. The bioenhancer can be administered with compounds from classes, such as, but not limited to, aminoacridines, aminoquinolines, anilides, anthracycline antibiotics, antiestrogens, benzofurans, benzhydryl compounds, benzazepines, cannabioids, cephalosporines, colchicine, cyclic peptides, dibenzazepines, epipodophyllotoxins, flavonoids, flavones, imidazole, isoquinolines, macrolides, opioids, phenylalkylamines, phenothiazines, piperazines, piperidines, polyethylene glycols, pyridines, pyridones, pyrimidines, pyrrolidines, quinazolines, quinolines, quinones, rauwolfia alkaloids, retinoids, salicylates, sorbitans, steroids, taxol, triazoles, unsaturated fatty acids, and vinca alkaloids. "Bioenhancer" as used herein also includes dihydropyridine, nitrogen mustard, and phenylpiperidine. The bioenhancer can also be made of a compound listed above.

The principal common characteristic of these compounds is that they act as inhibitors of P-gp drug transport. When the bioenhancers are used in sufficient amounts, the activity of P-gp will be reduced; in particular P-gp drug transport back into the intestinal lumen will be reduced. Sufficient amounts would include amounts necessary to increase integrated systemic concentrations over time of the drug used in conjunction with the bioenhancer. The concentration of bioenhancer required to produce a sufficient amount of bioenhancer for inhibition of P-gp drug transport varies with the delivery vehicle used for the bioenhancer and the drug. The luminal concentration of the bioenhancer should be related to the drug's and bioenhancer's relative affinities for P-gp and the drug concentration used. As the affinity of drug for P-gp increases, the required concentration of the appropriate bioenhancer will increase. Most bioenhancers of commercial application will decrease P-gp drug transport by at least 10%, more preferably by at least 50%, and even more preferably by at least 75%.

Several compounds that are themselves normally thought of as drugs can be used as bioenhancers, including calcium channel blockers, phenothiazines, quinidine, antimalarial agents, antiestrogenic and other steroids, and cyclosporine and other compounds listed in Table 2.

TABLE 2

Classes of P-Glycoprotein Substrates or Inihibitors with Specific Examples

| | |
|---|---|
| Antiarrhythmics | Local anesthetics |
| Amiodarone | Bupivacaine |
| Lidocaine | NSAIDs |
| Quinidine | Aspirin |
| Antibiotics & Antifungals | Phenothiazines |
| Cefoperazone | CREMOPHOR EL (polyethoxyl castor oil) |
| Ceftriaxone | |
| Erythromycin | TRITON X-100 |
| Itraconazole | (t-octylpheaoxypolyethoxyethyl) |
| Antimalarials & Antiparasites | TWEEN 80 (polyoxyethylenesorbitan monoole) |
| Chloroquine | |
| Emetine | Tricyclic antidepressants |
| Hydroxychloroquine | Desipramine |
| Quinacrine | Trazodone |
| Quinine | Miscellaneous |
| Calcium Channel Blockers | Dipyridamole |
| Bepridil | Reserpine |
| Diltiazem | Cyclosporine |
| Felodipine | Colchicine |
| Nifedipine | FK-506 |
| Nisoldipine | Liposomes |
| Nitrendipine | Quercetin |
| Tiapamil | SDZ PSC-833 |
| Verapamil | SDZ 280-446 |
| Cancer chemotherapeutics combination regimens | Terfenadine |
| | Tumor Necrosis Factor |
| Actinomycin D | Vitamin A |
| Daunorubicin | |
| Doxorubicin | |
| Mitomycin-C | |
| Taxol | |
| Trimetrexate | |
| Vinblastine | |
| Vincristine | |
| Hormones | |
| Aldosterone | |
| Clomiphene | |
| Cortisol | |
| Dexamethasone | |
| Prednisone | |
| Progesterone | |
| Tamoxifen | |

Any bioassay that determines whether a given compound has the inhibition characteristics required of a bioenhancer can be used to identify compounds that can be used in the practice of the present invention. A number of such assays are set out below.

In vitro P-gp Assays for Bioavailability

Everted Gut Assays

Everted intestine can be prepared by methods known in the art (Hsing et al. Gastrobentsrology 1992; 102:879–85). In these studies rat small intestines turned "inside out" (i.e. the mucosal (or luminal) surface turned outside and the serosal surface inside) are bathed in a drug containing solution with and without the addition of the bioenhancer. The serosal surface of the small intestine is bathed in a solution that is periodically monitored or changed for the purpose of drug or bioenhancer measurement. For instance the everted rat small intestines can be bathed in a physiological saline solution loaded with Rhodamine 123 (Rh123) and the flux of Rh 123 monitored into the serosal solution. The addition of a bioenhancer in this set-up will increase Rh 123 transport into the serosal solution. An increase in drug or Rh 123 bioavailability will be determined as follows:

$$\frac{X}{Y}(100)$$

where Y is the initial rate of Rh 123 transport, and X is the initial rate of rhodamine transport in the presence of a bioenhancer. The initial rates will be determined as a linear relationship between time and Rh 123 concentration in the luminal solution. Alternatively, the serosal side of rat small intestines is bathed with the drug or bioenhancer of interest and the mucosal solution is monitored, as described in Hsing et al. (1992).

Selection of a P-gp Inhibitor Based on Cell Growth Assays

This assay will be used to select candidate bioenhancers. Cells cultured with cytotoxic agents that are known P-gp transport substrates will be grown as controls in the absence of either drug or bioenhancer. The $appK_i$ (apparent inhibition constant) for cell growth by drugs will be determined by varying the drug concentration in the culture medium. The $appK_i$ will be expressed as the concentration of drug required to produce 50% inhibition of cell growth. Cells will also be grown in the presence of drug and bioenhancer. The bioenhancer will act to shift the $appK_i$ to lower drug concentrations necessary for inhibition of cell growth. Cells with MDR can be used in this assay as described in Hait, W. N., et al., Biochemical Pharmacology 1993; 45:401–406. The method sections of Hait, W. N., et al. (1993) are herein incorporated by reference. Preferred bioenhancers will decrease the $appK_i$ for a drug by at least 2 times, more preferably by at least 3 times, and even more preferably by at least 6 times.

Rhodamine (Rh 123) Cellular Assay of P-gp Drug Transport and Drug Bioavailability Rh 123 can be used in a cellular assay to monitor the bioavailability of drugs. Rh 123 transported by P-gp in this system acts as a drug, where P-gp pumps the Rh 123 out of the cell. Single cells or a population of cells can be monitored for the Rh 123 fluorescence which is indicative of P-gp transport. The cell types used will contain a P-gp transporter from a MDR strain such as those listed in Nielsen and Skovsgaard, Biochimica et Biophysica Acta 1993; 1139:169–183 and herein incorporated by reference. Cells are loaded with Rh 123 in the presence of 15 nanograms per ml to 500 nanograms per ml of Rh 123 in a physiologically compatible buffer such as 3-N-morpholinopropanesulfonic acid (MOPS) with the suitable concentrations of sodium, potassium, and calcium chloride and an energy source. The cells are loaded with Rh 123 for 30–60 minutes depending on the temperature (37° or room temperature ). The loaded cells are then washed and resuspended in buffer free of Rh 123. The efflux of Rh 123 can be determined using a fluorimeter. In the absence of any bioenhancer Rh 123 will be pumped out of the cell due to the action of P-gp, leading to a reduced amount of Rh 123 fluorescence from the cell.

Addition of a P-gp substrate or inhibitor either by preincubation after the cells have been washed with Rh 123 free buffer or during the efflux of Rh 123 from the cell will cause retention of Rh 123 within the cell. Retention of Rh 123 in the cell will be caused by the addition of a bioenhancer. Increased drug bioavailability is defined as the increase in Rh 123 retention within the cell. Compounds that increase Rh 123 retention are bioenhancers.

Rh 123 retention in the absence of a bioenhancer will be determined by total Rh 123 cell fluorescence minus background Rh 123 cell fluorescence. An increase in drug bioavailability due to the addition of the bioenhancer will be the percentage increase in Rh 123 fluorescence retention as described by:

$$\frac{X}{Y}(100)$$

where X equals Rh 123 fluorescence in the presence of the bioenhancer minus the background Rh 123 fluorescence and Y equals the Rh 123 fluorescence in the absence of the bioenhancer minus the background Rh 123 fluorescence.

The background Rh 123 fluorescence can be measured in a variety of ways including, but not limited to, the residual amount of Rh 123 fluorescence at the end of the experiment, the residual amount of Rh 123 fluorescence remaining based on an extrapolation of first order rate kinetics describing the efflux of Rh 123 from the cell, the residual amount of Rh 123 fluorescence in the presence of a sufficient amount of membrane detergents such as triton or digitonin, or the amount of Rh 123 fluorescence in the presence of a potassium-valinomycin clamp.

The addition of both a second drug and a bioenhancer to the Rh 123 assay will not necessarily cause an increased amount of Rh 123 retention compared to the presence of either the bioenhancer alone or the second drug alone. This is because Rh 123 retention can already be very high due to the second drug or bioenhancer concentration. Extra retention due to the addition of either the second drug or the bioenhancer can be difficult to measure above the signal for Rh 123 in the presence of the second drug or bioenhancer alone. However, once it has been determined that the drug (or second drug alone) increases Rh 123 fluorescence, i.e. decreases Rh 123 efflux, it can be assumed that the drug (or second drug alone) is transported by the P-gp transport system.

Vesicle Assays of P-gp Activity and Drug Bioavailability

A particularly preferred assay uses brush border membranes. Brush border membrane vesicles are prepared from the small intestine by methods known in the art, such as, Hsing, S. et al., Gastroenterology 1992; 102:879–885. The vesicles will be assayed for the presence of P-gp by using monoclonal antibodies directed to P-gp either using SDS page gel electrophoresis and western blotting techniques or using immunochemistry and electromicroscopy. Vesicles containing P-gp will be used for drug transport assays.

Drug transport assays consist of measuring the transport of drugs into the vesicles in an adenosine triphosphate (ATP) dependent fashion. Uptake of the drug in the presence of ATP will be monitored using fluorescence or absorbance techniques, for instance using Rh 123 as the fluorescent drug transported into the interior of the vesicle. Radioactively labeled drugs can also be used to monitor drug transport into the interior of the vesicle using a filter wash system. The addition of ATP will induce the transport of the drug into the vesicle and will increase drug transport compared to passive diffusion of the drug into the vesicle interior. Addition of non-hydrolyzable analogs of ATP such as ATP gamma S or adenosine monophosphate para-nitrophenol (AMP-PNP) will not produce an ATP dependent influx of drug into the vesicle. Thus, the introduction of a non-hydrolyzable nucleotide can be used as a control to monitor whether drug transport has actually occurred due to ATP hydrolysis from the P-gp transport system.

The addition of a bioenhancer to this assay system using a fluorescent drug or a radioactive drug and monitoring its uptake, will reduce the uptake of the drug into the interior of the vesicle with the addition of ATP. This reduction in drug transport represents an increase of the bioavailability of the drug. The vesicles transporting drugs in an ATP dependent fashion are oriented with the cystolic face of the P-gp accessible to the ATP. It is these vesicles that hydrolyze the ATP and transport the drug into the interior of the vesicle. The interior of the vesicle in turn corresponds to the luminal surface or the apical membrane of the brush border cells. Thus, transport into the lumen of the vesicle or interior of the vesicle corresponds to transport into the lumen of the gut. A decrease in the transport of the lumen of the vesicle is the equivalent of increasing net drug absorption and increasing the drug bioavailability.

P-gp ATPase Assays of P-gp Activity and Drug Bioavailability

P-gp molecules can be isolated in vesicles suitable for measuring ATP'ase activity. P-gp ATP'ase activity will be measured in the presence of other types of ATP'ase inhibitors, such as, but not limited to, sodium potassium ATPase inhibitors (ouabain and vanadate), mitochondrial ATP'ase inhibitors such as oligomycin, and alkaline phosphatase inhibitors. The ATP'ase assays will also be conducted in the absence of sodium and potassium to eliminate background sodium and potassium ATP'ase activity. ATP'ase activity will be measured as ATP'ase activity dependent on the presence of a drug such as daunomycin. ATP'ase activity will be measured using ATP or hydrolyzable ATP analogs such para-nitrophenolphosphate. The production of product will be monitored using phosphate assay procedures of those of Yoda, A. and Hokin, L., *Biochem. Biophys. Res. Comm.* 1970; 40:880–886 or by monitoring phosphatase activity as recognized in the literature.

An increase in P-gp ATPase activity due to the addition of a drug is recognized as an increase in drug bioavailability. P-gp molecules located in the brush border membrane vesicles are oriented so the cytosolic portion of the molecule finds and hydrolyzes ATP. It is these P-gp molecules that will give rise to the drug dependent ATPase activity. Bioenhancer that is able to stimulate the ATPase activity will be able to compete with the drug for the P-gp transport system. Such bioenhancers will decrease P-gp drug transport due to their increased ability to stimulate P-gp activity. Bioenhancers can also inhibit drug dependent P-gp ATP'ase activity without stimulating P-gp ATP'ase activity thus, inhibiting drug transport.

Another manner of determining the amount of bioenhancer appropriate for an oral formulation is based on the $K_i$ of the specific inhibitor (for whichever binding is being measured). An appropriate amount of inhibitor is one that is sufficient to produce a concentration of the bioenhancer in the lumen of the gut of the animal of at least 0.1 times the $K_i$ of the bioenhancer.

In all of these cases, the goal of selecting a particular concentration is increased bioavailability of the pharmaceutical compound that is being administered. Thus, a desirable goal is to provide integrated systemic concentrations over time of the pharmaceutical compound in the presence of the inhibitor that is greater than the integrated systemic concentrations over time of the pharmaceutical compound in the absence of the inhibitor by at least 10% of the difference between bioavailability in its absence and complete oral bioavailability. Preferred is attaining of "complete bioavailability," which is 100% systemic bioavailability of the administered dosage.

Screening Assay for Bioenhancers

In summary, the various techniques described above for screening candidate bioenhancer compounds for activity by assaying for inhibition in the gut of a mammal of activity of a cytochrome P450 enzyme or of transport by P glycoprotein are all generally useful as methods of identifying compounds that are useful for increasing bioavailability of a drug in a mammal. In all of these assays, the best bioenhancers are those compounds selected from the candidate compounds being tested that best inhibit either transport or enzymatic destruction (preferably the latter) of a tested drug in the gut of the mammal (either by direct testing in vivo or by a test that predicts such activity). When testing for inhibition of activity of a cytochrome enzyme, assays that detect inhibition of members of a cytochrome P450 3A family (for a particular mammal, particularly human) are preferred. Although in vivo assays are preferred, because of the direct relationship between the measurement and gut activity, other assays, such as assays for inhibition of cytochrome P450 activity in isolated enterocytes or microsomes obtained from enterocytes of the mammal in question or for inhibition of cytochrome P450 in a tissue or membrane from the gut of said mammal, are still useful as screening assays. The same ordering of preferred screening assays (i.e., in vivo being preferred over in vitro) is also preferred for screening of inhibition of P-gp transport. Screening by assaying for both inhibitions is preferred, with inhibition of cytochrome P450 activity generally being more important than that of P-gp-mediated transport.

Coadministration and Delivery of Bioenhancers

Increase in Drug Bioavailability with Coadministration of a Bioenhancer and a Drug The present invention will increase the bioavailability of the drug in the systemic fluids or tissues by co-administering the bioenhancer with a drug. "Co-administration" includes concurrent administration (administration of the bioenhancer and drug at the same time) and time varied administration (administration of the bioenhancer at a time different from that of the drug), as long as both the bioenhancer and the drug are present in the gut lumen and/or membranes during at least partially overlapping times. Systemic fluids or tissues refer to drug concentration measured in blood, plasma or serum, and other body fluids or tissues in which drug measurements can be obtained.

Delivery Vehicles Provide For Coadministration

Coadministration can vary in the type of delivery vehicle. The bioenhancer and the drug can use different delivery vehicles such as, but not limited to, time release matrices, time release coatings, companion ions, and successive oral administrations. Alternatively, the drug and the bioenhancer can be formulated with different coatings possessing different time constants of bioenhancer and drug release. The use of bioenhancers also applies to epithelia tissues other than the gut. Aspects of the invention used in the gut are appropriately used in other types of epithelia. For example, CYP 3A enzymes and P-glycoprotein have also been demonstrated in the skin and bioenhancers used in transdermal formulations would increase drug bioavailability to systemic fluids and tissues. Such applications are included as part of the invention herein because of inhibition by bioenhancers of CYP 3A enzymes and P-glycoprotein in epithelia other than the gut.

Formulations of Bioenhancers

In some embodiments, the bioenhancer comprises a cytochrome-P450-3A-inhibiting compound and a separate P-glycoprotein-inhibiting compound. In other cases, the bioenhancer comprises a single compound that inhibits both CYP3A and P-glycoprotein, or just one of the two processes. The bioenhancer is preferably present as a counter ion of the pharmaceutical compound in order to ensure that the bioenhancer is present at maximum concentration in the presence of the drug that it is protecting.

The cytochrome P450 3A family of enzymes and the P-gp transporting protein both have a wide range of substrates, and thus potential inhibitors, as exemplified by the variety of structures present in compounds that can act as inhibitors as set forth above.

The invention is carried out in part by formulating an oral pharmaceutical composition to contain a bioenhancer. This is accomplished in some embodiments by admixing a pharmaceutical compound, a pharmaceutical carrier, and a bioenhancer comprising an inhibitor of P-glycoprotein-mediated membrane transport or an inhibitor of a cytochrome P450 3A enzyme, the bioenhancer being present in sufficient amount to provide integrated systemic concentrations over time of the compound as measured by AUC's greater than the integrated systemic concentrations over time of the compound in the absence of the composition when the pharmaceutical composition is administered orally to an animal being treated with the pharmaceutical composition. A pharmaceutical carrier increases drug solubility or protects drug structure or aids in drug delivery or any combination thereof.

Pharmaceutical compositions produced by the process described herein are also part of the present invention.

In addition to use with new formulations, the present invention can also be used to increase the bioavailability of the active compound of an existing oral pharmaceutical composition. When practiced in this manner, the invention is carried out by reformulating the existing composition to provide a reformulated composition by admixing the active compound with a bioenhancer comprising an inhibitor of a cytochrome P450 3A enzyme or an inhibitor of P-glycoprotein-mediated membrane transport, the bioenhancer being present in sufficient amount to provide integrated systemic concentrations over time of the compound when administered in the reformulated composition greater than the integrated systemic concentrations over time of the compound when administered in the existing pharmaceutical composition. All of the criteria described for new formulations also apply to reformulation of old compositions. In preferred aspects of reformulations, the reformulated composition comprises all components present in the existing pharmaceutical composition plus the bioenhancer, thus simplifying practice of the invention, although it is also possible to eliminate existing components of formulations because of the increase in bioavailability. Thus, the invention also covers reformulated compositions that contain less than all components present in the existing pharmaceutical composition plus the bioenhancer. However, this invention does not cover already existing compositions that contain a component which increases bioavailability by mechanisms described in this specification (without knowledge of the mechanisms), should such compositions exist.

Traditional formulations can be used with bioenhancers. Optimal bioenhancer doses can be determined by varying the coadministration of bioenhancer and drug in time and amount dependent fashion and monitoring bioavailability. Once the optimal bioenhancer dose is established for a drug the formulation (bioenhancer, drug and formulation composition(s)) is tested to verify the increased bioavailability. In the case of time or sustained release formulations it will be preferred to establish the optimal bioenhancer dose using such formulations from the start of the bioavailability experiments.

EXAMPLE—QUANTITATION OF BIOENHANCER IN VIVO

Cyclosporin (CYA) Bioavailability in the Absence and Presence of Ketoconazole (KC) As A Bioenhancer 1. General Design of Methodology:

Six male/female healthy volunteers served as subjects for the procedure. Pre-procedure laboratory tests, physical examinations, and consent was obtained at least five days prior to the procedure date.

The procedure was performed in two phases. During the initial phase (I), baseline oral and intravenous pharmacokinetic parameters were established. Phase II consisted of ketoconazole administration and oral/intravenous pharmacokinetic procedures. Each phase followed identical procedures: after an overnight fast, subjects were admitted for initial CYA pharmacokinetics procedures. The order of CYA route of administration was randomized during phase I, and the same order was maintained in phase II. After the insertion of an indwelling catheter, each subject received an oral or intravenous dose of CYA with 5 mL blood draws obtained at 0, 15, 30, 45, and 60 minutes, then 2, 3, 4, 5, 6, 8, 10, 12, 14, and 24 hours (total volume of blood: 300 mL). During the intravenous infusion, contralateral catheters were inserted. Intravenous CYA was administered over 2.5 hours by AVI infusion pump. After completing the i.v. infusion, the infusion catheter was removed. Subjects either returned to the testing location in the morning for each 24 hour blood draw or stayed overnight in the testing location.

During phase I, subjects received oral or i.v. CYA (8 mg/kg and 2.5 mg/kg, respectively) and followed the above procedures (Day 1). After a three day washout period (Day 5), subjects received CYA i.v. or p.o. depending on initial randomization. Blood samples were drawn as described above. When subjects returned to the testing location for the 24 hour blood draw (Day 6), they were given KC 200 mg and instructed to take one tablet daily at 10 PM for eight days. The last dose of ketoconazole was taken the night of procedure day 14, just before the last pharmacokinetic procedure day.

In study sections designed to evaluate Ketoconazole's effects (Phase II) on both intravenous and oral CYA metabolism, dosing of the bioenhancer and the drug (CYA) were separated by approximately 10 hours.

During phase II (Day 11), subjects were admitted to the testing location after an overnight fast for further CYA pharmacokinetic procedures. Subjects received either a single oral dose of CYA at a reduced dose of 2 mg/kg or intravenous CYA (0.6 mg/kg) depending on the previous randomization schedule. Blood samples were drawn as described above. After a three day washout period, on Day 15, subjects received the oral (2 mg/kg) or i.v. (0.6 mg/kg) dose, again depending on the initial randomization schedule. Blood samples were drawn as described above.

In phase II, in healthy volunteers, dosing of CYA in the presence of the enhancer was reduced from that administered when no bioenhancer was present for safety considerations.

The total volume of blood drawn for this procedure was 380 mL (pre/post labs and pharmacokinetic procedures).

2. Sample and Data Analysis:

Whole blood samples were assayed for CYA and metabolites (AM1, AM4N, AM9, AM1c9) by HPLC. Pharmacokinetic parameters, including bioavailability, were obtained from data and compared for differences between baseline (−KC) and inhibition (+KC).

3. Subject Selection Criteria:

a. Healthy adult volunteers were used to minimize interpatient variation in response to drug administration, which can occur with hepatic or renal dysfunction, and to minimize risks associated with drug administration.

b. Eight healthy male or female subjects were recruited for this procedure to assure that at least six subjects completed both phases.

c. Inclusion Criteria:

>than 18 years of age

Weight not more than 10% above or below the ideal body weight for age, height and weight. (Metropolitan Life Insurance Co. tables)

Good health on the basis of history and physical exam.

No history of cardiovascular, renal, hepatic, gastrointestinal, respiratory, hematologic disease, or other diseases which could affect the distribution, absorption, metabolism, or excretion of either procedure drugs.

Have laboratory tests within normal limits.

Ability to provide written and informed consent.

d. Exclusion Criteria:

Use of any drugs, including both prescription and chronic over-the-counter medications within one week of the procedure. Specifically, use of antacids, $H_2$-antagonists, or other agents known to decrease KC absorption or interactions with CYA.

Participation in experimental drug procedure within one month preceding the procedure.

History of hypersensitivity of KC, azole-antifungal agents, or CYA.

History of myxedema, hyperthyroidism, hepatic disease, hepatitis, alcohol, or recreational drug use, cardiac arrhythmias, seizures, tobacco, or any other condition which can alter drug metabolism, absorption, or distribution.

4. Subject Recruitment:

Subjects were recruited from the population in and around a university campus. Potential subjects were screened for their fitness to participate in the procedure within 5 days prior to procedure date. The screening procedure included the following: medical and drug histories, physical exam and baseline laboratory procedures (hemoglobin, hematocrit, RBC, WBC, differential, platelets, potassium, chloride, bicarbonate, serum creatinine, BUN, glucose, albumin, total bilirubin, alkaline phosphatase, AST, ALT, cholesterol, HOL, LOL, and a urine pregnancy test when female volunteers were used).

5. Specific Procedures:

a. At least five days prior to the procedure date, a 40 mL blood sample was drawn from each subject for baseline laboratory procedures as stated above. At this time a history and physical exam was performed.

b. The procedure was divided into two phases. During phase I, baseline CYA pharmacokinetics after intravenous and oral dosing were established. During phase II, subjects were given eight days of KC therapy, and post-KC intravenous and oral CYA pharmacokinetic procedures were performed. Subjects were randomized to receive an oral or i.v. dose as the initial route of administration and followed this randomization throughout the procedure.

Day 1: Subjects were admitted to the testing location at 07:00 after an overnight fast from 22:00 the previous evening. An indwelling polyethylene catheter with a teflon obturator was inserted aseptically into the forearm vein for blood withdraw. Immediately prior to drug administration, a 5 mL blood sample was collected. CYA was then administered orally (8 mg/kg) or intravenously (2.5 mg/kg over 2.5 hours) based on body weight. Five milliliter blood samples were drawn at the following times post during administration: 15, 30, 45, 60 minutes and 2, 3, 4, 5, 6, 8, 10, 12, 14, and 24 hours. Subjects returned to the testing location the following day (Day 2) for the 24 hour blood draw (peripheral venipuncture). Whole blood was analyzed for parent drug and metabolites. Some samples were frozen prior to extraction. Breakfast, lunch, a light snack, and dinner were supplied during all days spent in the testing location. All subjects were given oral CYA with chocolate milk to ensure adequate absorption and to minimize variability in absorption. Subjects were allowed to drink water freely.

Day 5: After a three day wash-out period, subjects were again admitted to the testing location, and identical procedures were followed as described above in Day 1 except that subjects received CYA by the alternate route of administration not used previously on Day 1. Subjects receiving CYA by the i.v. route had the i.v. catheter removed after the infusion was completed. Blood samples were drawn as described above.

Day 6: When returning for the 24 hour blood draw, subjects received a 100 mg dose of ketoconazole (half-dose) and were observed for one hour, the other 100 mg being taken at 10 pm that evening. Each subject was instructed to take one 200 mg tablet each evening at 10 pm with food. Subjects were instructed to take KC for a total of eight days. The last dose of KC was taken on Day 14.

Day 11: The procedure went forward as described for Day 1 with the exception of CYA dosing. Subjects received an oral dose of 2 mg/kg of CYA or an i.v. dose of 0.6 mg/kg over 2.5 hours. Blood samples were drawn as previously described. An identical diet was provided to minimize changes in CYA absorption.

Day 15: After the three day wash-out period, subjects were admitted to the testing location and received the final CYA i.v. or oral dose. Blood samples were drawn as previously described. The 24 hour blood draw included an additional 40 mL to perform post-procedure laboratory tests. Prior to discharge, each subject underwent a physical exam and history to detect any adverse reactions due to drugs or catheter insertion.

Since CYA absorption can be highly variable, especially with diet content, food outside of the procedure diet was not permitted. All meals (breakfast, lunch, snack, dinner) were supplied on all procedure days.

F. Results

KC inhibited the metabolism of cyclosporine (CYA), resulting in elevated CYA levels. CYA as a single dose was administered orally and intravenously, pre- and post-KC treatment to 6 normal healthy volunteers. The mean pre-KC bioavailability (F) was 22.2% compared to 62.0% post-KC (P<0.003). Utilizing $F_{hepatic}=1-ER$, where $ER=CL_{IV}$/hepatic blood flow (1.28 L/hr/kg), F can be broken down into its components: $F_{hepatic} \times F_{abs} \times F_{gut}$. $F_{abs} \times F_{gut}$ increased significantly post-KC (68.5%) compared to pre-KC (26.2%) (P<0.006), whereas $F_H$ changed minimally, 90% $^{post-KC}$ vs 86% $^{pre-KC}$ (P=0.10). CYA is well absorbed (>62%) by the gut under these conditions.

The interaction between CYA and ketoconazole is also expressed graphically in FIG. 1. Subject CYA levels were measured after IV administration of CYA pre-KC treatment (pre-IV) and post-KC treatment (post-IV). Subject CYA levels were also measured after oral administration of CYA pre-KC treatment (pre-PO) and post-KC treatment (post-PO). The increase in CYA concentration was greatest post-KC treatment of orally administered CYA.

This example demonstrates the effect of intestinal P450 enzymes on the bioavailability of CYA. It shows that intestinal P450 enzymes are important determinants of the bioavailability of CYA and other agents which undergo significant metabolism by P450 enzymes.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. A method for increasing bioavailability of an orally administered pharmaceutical compound, which comprises:
orally coadministering to a mammal in need of treatment by said pharmaceutical compound (1) said pharmaceutical compound and (2) a bioenhancer, said bioenhancer comprising an inhibitor of a cytochrome P450 3A enzyme or an inhibitor of P-glycoprotein-mediated membrane transport in normal gut tissue, said bioenhancer being active only in the gut when administered orally and being present in sufficient amount to provide bioavailability of said compound in the presence of said bioenhancer greater than bioavailability of said compound in the absence of said bioenhancer.

2. The method of claim 1, wherein said bioenhancer comprises an inhibitor of a cytochrome P450 3A enzyme and said inhibitor is a hydrophobic molecule.

3. The method of claim 1, wherein said bioenhancer comprises an inhibitor of a cytochrome P450 3A enzyme and said inhibitor is present at a concentration in the gut of said mammal equal to or greater than a concentration of said bioenhancer that reduces conversion of cyclosporine to hydroxylated products by 10%, compared to controls, in an assay system containing 100 μg human liver or enterocyte microsomes, 25 μM cyclosporine, and an NADPH regenerating system in 100 μl of 0.1 M sodium phosphate buffer, pH 7.4.

4. The method of claim 1 wherein said amount of said bioenhancer is sufficient to produce a concentration of said bioenhancer in the lumen of the gut of said mammal of at least 0.1 times said $K_i$ or apparent $K_i$ of the bioenhancer.

5. The method of claim 1, wherein bioavailability in the presence of said inhibitor is greater than bioavailability of said compound in its absence by at least 10% of the difference between bioavailability in its absence and complete oral bioavailability.

6. The method of claim 1, wherein said bioenhancer comprises an inhibitor of P-glycoprotein-mediated membrane transport and said inhibitor is a hydrophobic molecule comprising two co-planar aromatic rings or a positively charged nitrogen group, or a carbonyl group.

7. The method of claim 1, wherein said bioenhancer comprises an inhibitor of P-glycoprotein-mediated membrane transport and said inhibitor is present at concentrations equal to or greater than concentrations that reduce transport of Rh 123 by P-glycoprotein in brush border membrane vesicles or P-gp-containing cells by 10%.

8. The method of claim 1, wherein said bioenhancer reduces inter-individual variability of said bioavailability of said pharmaceutical compound.

9. The method of claim 1, wherein said bioenhancer reduces intra-individual variability of said bioavailability of said pharmaceutical compound.

10. The method of claim 1, wherein said bioenhancer comprises an inhibitor of a cytochrome P450 3A enzyme and a separate inhibitor of P-glycoprotein-mediated membrane transport.

11. The method of clam 1, wherein said bioenhancer comprises a single compound that inhibits both a cytochrome P450 3A enzyme and P-glycoprotein-mediated membrane transport.

12. A method for increasing bioavailability of an orally administered pharmaceutical compound, which comprises:
orally coadministering to a mammal in need of treatment by said pharmaceutical compound (1) said pharmaceutical compound and (2) a bioenhancer, said bioenhancer comprising an inhibitor of a cytochrome P450 3A enzyme or an inhibitor of P-glycoprotein-mediated membrane transport in normal gut tissue, said bioenhancer being active only in the gut when administered orally and being present in sufficient amount to provide bioavailability of said compound in the presence of said bioenhancer greater than bioavailability of said compound in the absence of said bioenhancer, wherein whether a bioenhancer is active only in the gut is determined by measuring change in bioavailability of said compound when orally coadministered to said mammal with said bioenhancer, measuring change in integrated systemic concentration of said compound when said compound is intravenously administered and said bioenhancer is orally coadministered, and determining that said change in said bioavailability when said compound is orally administered is a statistically significant increase and said change in said integrated systemic concentration when said compound is intravenously administered is not statistically significant.

13. The method of claim 12, wherein said change in said bioavailability when said pharmaceutical compound is orally coadministered with said bioenhancer has a statistical p-value of no more than 0.006.

14. The method of claim 12, wherein said change in said integrated systemic concentration when said pharmaceutical compound is intravenously administered and said bioenhancer is orally coadministered has a statistical p-value of no less than 0.10.

15. The method of claim 12, wherein said change in said bioavailability when said pharmaceutical compound is orally coadministered with said bioenhancer has a statistical p-value of no more than 0.006 and said change in said integrated systemic concentration when said pharmaceutical compound is intravenously administered and said bioenhancer is orally coadministered has a statistical p-value of no less than 0.10.

16. The method of claim 12, wherein said bioenhancer comprises an inhibitor of a cytochrome P450 3A enzyme and a separate inhibitor of P-glycoprotein-mediated membrane transport.

17. The method of claim 12, wherein said bioenhancer comprises a single compound that inhibits both a cytochrome P450 3A enzyme and P-glycoprotein-mediated membrane transport.

18. The method of claim 12, wherein said pharmaceutical compound comprises an acetanilide, aminoacridine, aminoquinoline, anilide, anthracycline antibiotic, antiestrogen, benzazepine, benzhydryl compound, benzodiazapine, benzofuran, cannabinoid, cephalosporine, colchicine, cyclic peptide, dibenzazepine, digitalis glycoside, dihydropyridine, epipodophyllotoxin, ergot alkaloid, imidazole, isoquinoline, macrolide, naphthalene, nitrogen mustard, opioid, oxazine, oxazole, phenothiazine, phenylalkylamine, phenylpiperidine, piperazine, piperidine, polycyclic aromatic hydrocarbon, pyridine, pyridone, pyrimidine, pyrrolidine, pyrrolidinone, quinazoline, quinoline, quinone, rauwolfia alkaloid, retinoid, salicylate, steroid, stilbene, sulfone, sulfonylurea, taxol, triazole, tropane, or vinca alkaloid.

* * * * *

UNITED STATES PATENT AND TRADEMARK OFFICE
CERTIFICATE OF CORRECTION

PATENT NO. : 6,004,927
DATED : December 21, 1999
INVENTOR(S) : Leslie Z. Benet, et al.

It is certified that error appears in the above-identified patent and that said Letters Patent is hereby corrected as shown below:

At column 1, after the title insert:

--Acknowledgement

This invention was made with U.S. Government support under Grant No. GM 26691, awarded by the National Institutes of Health. The Government has certain rights to this invention.--

At column 16, Table 2, under the heading "Phenothiazines" at line 10, insert the heading --Surfactant / solvents--.

At column 16, Table 2, after "CREMOPHOR EL" at lines 11-12, replace "polyethoxyl castor oil" with --polyethoxylated castor oil--.

At column 16, Table 2, after "TRITON X-100" at lines 13-14, replace "t-octylpheaoxypolyethyl" with --t-octylphenoxypolyethoxyethanol--.

At column 16, Table 2, under the heading "TWEEN 80" at lines 15-16, replace "polyoxyethylenesorbitan monoole" with --polyoxyethylenesorbitan monooleate--.

UNITED STATES PATENT AND TRADEMARK OFFICE
CERTIFICATE OF CORRECTION

PATENT NO. : 6,004,927
DATED : December 21, 1999
INVENTOR(S) : Leslie Z. Benet, et al.

It is certified that error appears in the above-identified patent and that said Letters Patent is hereby corrected as shown below:

At column 16, line 56 replace "Gastrobentsrology" with --*Gastroenterology*--.

At column 19, line 17 replace the two occurrences of "ATP'ase" with --ATPase--.

At column 19, lines 18, 21, 22 and 24 replace "ATP'ase" with --ATPase--.

At column 19, line 25 replace the two occurrences of "ATP'ase" with --ATPase--.

At column 19, lines 27, 43 and 44, replace "ATP'ase" with --ATPase--.

At column 19, lines 44-45, delete "activity thus, inhibiting drug transport" and replace with --activity. Thus, such bioenhancers also inhibit drug transport.--.

At column 3, line 19 replace "taxol" with --taxol (paclitaxel)--.

At column 28, in claim 18 at line 4, replace "taxol" with --paclitaxel--.

Signed and Sealed this

Ninth Day of January, 2001

*Attest:*

Q. TODD DICKINSON

*Attesting Officer*     *Commissioner of Patents and Trademarks*